US011918671B2

(12) United States Patent
Kruck et al.

(10) Patent No.: US 11,918,671 B2
(45) Date of Patent: Mar. 5, 2024

(54) MULTI-TONE HAIR DYEING METHOD IN THREE STEPS

(71) Applicant: Henkel AG & Co. KGaA, Duesseldorf (DE)

(72) Inventors: Constanze Kruck, Grevenbroich (DE); Melanie Moch, Dormagen (DE); Daniela Kessler-Becker, Leverkusen (DE); Sandra Hilbig, Bochum (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 17/782,090

(22) PCT Filed: Oct. 13, 2020

(86) PCT No.: PCT/EP2020/078717
§ 371 (c)(1),
(2) Date: Jun. 2, 2022

(87) PCT Pub. No.: WO2021/110306
PCT Pub. Date: Jun. 10, 2021

(65) Prior Publication Data
US 2023/0031764 A1  Feb. 2, 2023

(30) Foreign Application Priority Data

Dec. 3, 2019 (DE) .......................... 102019218788.9

(51) Int. Cl.
| | | |
|---|---|---|
| A61Q 5/10 | (2006.01) | |
| A61K 8/22 | (2006.01) | |
| A61K 8/24 | (2006.01) | |
| A61K 8/41 | (2006.01) | |
| A61K 8/49 | (2006.01) | |
| A61Q 5/08 | (2006.01) | |

(52) U.S. Cl.
CPC ................ *A61K 8/494* (2013.01); *A61K 8/22* (2013.01); *A61K 8/24* (2013.01); *A61K 8/415* (2013.01); *A61Q 5/08* (2013.01); *A61Q 5/10* (2013.01); *A61K 2800/884* (2013.01)

(58) Field of Classification Search
CPC . A61K 8/494; A61K 8/22; A61K 8/24; A61K 8/415; A61K 2800/884; A61K 8/4946; A61K 8/4953; A61K 8/33; A61Q 5/08; A61Q 5/10
USPC ............................................................ 8/405
See application file for complete search history.

(56) References Cited

U.S. PATENT DOCUMENTS

| | | | |
|---|---|---|---|
| 8,268,015 B2 * | 9/2012 | Oberkobusch ........... | A61K 8/40 8/405 |
| 2011/0247644 A1 * | 10/2011 | Oberkobusch ....... | A61K 8/4953 424/62 |

FOREIGN PATENT DOCUMENTS

| | | |
|---|---|---|
| DE | 102008061863 A1 | 4/2010 |
| EP | 2014275 A2 | 1/2009 |
| WO | 2005051336 A1 | 6/2005 |
| WO | 2005120445 A2 | 12/2005 |
| WO | 2010046256 A2 | 4/2010 |
| WO | 2010072512 A2 | 7/2010 |
| WO | 2016030189 A1 | 3/2016 |

OTHER PUBLICATIONS

STIC Search Report dated May 18, 2023.*

* cited by examiner

*Primary Examiner* — Eisa B Elhilo
(74) *Attorney, Agent, or Firm* — Lorenz & Kopf, LLP

(57) ABSTRACT

A method for dyeing hair is disclosed. The method comprises (1) treating hair with an oxidative colorant agent (A); (2) subsequent to (1), treating the hair with a CH-acidic hair dyeing agent (B); and (3) subsequent to (2), treating the hair with a cosmetic decolorizing agent (Ox). The method comprises a time interval between (1) and (2) of from about 1 minute to about 1.5 months, and a time interval between (2) and (3) of from about 1 minute to about 1.5 months. A process for multitonal dyeing of hair is also disclosed. The process comprises preparing an oxidative colorant agent (A); treating hair with the agent (A) to give a colored hair; preparing a CH-acidic hair dyeing agent (B); treating the colored hair with the agent (B) to give a dyed hair; and treating the dyed hair with a cosmetic decolorizing agent (Ox) to give a multitonal dyed hair.

20 Claims, No Drawings

MULTI-TONE HAIR DYEING METHOD IN THREE STEPS

CROSS-REFERENCE TO RELATED APPLICATION

This application is a U.S. National-Stage entry under 35 U.S.C. § 371 based on International Application No. PCT/EP2020/078717, filed Oct. 13, 2020, which was published under PCT Article 21(2) and which claims priority to German Application No. 102019218788.9, filed Dec. 3, 2019, which are all hereby incorporated in their entirety by reference.

TECHNICAL FIELD

The present disclosure relates to a method for the multi-tonal dyeing of hair, in which the hair is first oxidatively treated with a permanent hair dye (method step 1), then overdyed with a CH-acid dyeing agent based on reactive carbonyl compounds and CH-acid compounds in a second color (method step 2) and the CH-acid dyeing is later decolorized again with an alkaline hydrogen peroxide-comprising composition (method step 3) until the color shade of method step 1 is achieved.

Human hair today is treated in many ways with hair cosmetic preparations. This includes, for example, cleaning the hair with shampoos, its care and regeneration with conditioners and treatments, and bleaching, coloring and shaping the hair with dyes, coloring agents, waving agents and styling products. Therefore, agents that change or nuance the color of the hair play a prominent role.

BACKGROUND

Changing the color of hair represents an important area of modern cosmetics. This allows the appearance of the hair to be adapted to current fashion trends as well as to the individual wishes of the person. In addition, the desire to preserve the natural color of hair even in old age, and therefore means to conceal gray hair, is becoming more and more pronounced among consumers.

Oxidative hair dyes comprise at least one developer component, also known as oxidation base, and usually at least one coupler component as color-changing active ingredients. Coupler and developer components are also referred to as oxidation dye precursors (OFV). If necessary, one or more direct dyes are also included as shading agents.

Before their application to human hair, hair dyes in solid or paste form are usually mixed with a dilute aqueous hydrogen peroxide solution. The resulting mixture is then applied to the hair and rinsed after a certain exposure time. The exposure time on the hair to achieve a total coloration is usually between about 30 and 40 minutes.

To achieve a sufficient coloring effect, the ready-to-use oxidative dyes are usually strongly alkaline, with a pH value between 8 and 10.5. Such high pH values are necessary to ensure opening of the outer cuticle layer and thus allow penetration of the active substances (hydrogen peroxide, OFV) into the hair. Under the influence of hydrogen peroxide, the OFV oligomerize and form the final dyes. Due to their size, these dye molecules remain fixed inside the hair fiber. Such oxidative hair dyes usually give the hair a four to six week long lasting coloration, which is therefore also called "permanent". Usually, hair dyeing achieved by oxidation has good wash, rub and light fastness.

In addition, it is also possible to achieve colorations with almost permanent properties by non-oxidative agents using certain cationic azo dyes, such as Basic Orange 31, Basic Red 51 or Basic Yellow 87. A quick color proof of these dyes is not possible.

Other direct dyes, especially the anionic direct dyes, but also the non-ionic direct dyes, show disadvantages such as a strong coloring of the scalp or additive color development, so that on oxidatively dyed hair in a dark shade no temporary effects in a lighter shade are possible.

Of course, with a further oxidative coloring or also with an oxidative bleaching using oxidation enhancers, such as persalts, effects can be subsequently applied to the oxidatively precolored hair; however, these are then not temporary, but—just like the first oxidation coloring—permanent. In addition, a second oxidative hair treatment would severely damage the hair.

What is usually an advantage, however, is contrary to the desire for a quick, easy change of hair color. Many consumers would also like a temporary color change, for example for parties or similar occasions, which has reliable rub fastness and possibly also color fastness, at least to a rain shower, for the duration of the special occasion. Since the hair coloration chosen for the special occasion can be very conspicuous and not appropriate for everyday life and therefore undesirable, there is a desire for a temporary coloration that, on the one hand, achieves additional attractive color effects on oxidatively colored hair, but can also be easily removed completely after the end of the occasion without negatively affecting the existing oxidatively achieved hair color.

BRIEF SUMMARY

A method for dyeing hair is provided. The method comprises (1) treating hair with an oxidative colorant agent (A); (2) subsequent to (1), treating the hair with a CH-acidic hair dyeing agent (B); and (3) subsequent to (2), treating the hair with a cosmetic decolorizing agent (Ox). The method comprises a time interval between (1) and (2) of from about 1 minute to about 1.5 months, and a time interval between (2) and (3) of from about 1 minute to about 1.5 months. The CH-acidic hair dyeing agent (B) has a pH of from about 7 to about 10, measured at 22° C., and comprises the product of mixing together three agents (B1), (B2), and (B3). Agent (B1) comprises at least one reactive carbonyl compound in a cosmetic carrier and is free from CH-acidic compounds. Agent (B2) comprises at least one CH-acidic compound in a cosmetic carrier and is free from reactive carbonyl compounds. Agent (B3) comprises at least one alkalizing agent. The at least one CH-acidic compound of Agent (B2) is selected from compounds of the formula (CH-1) and/or compounds of the formula (CH-2):

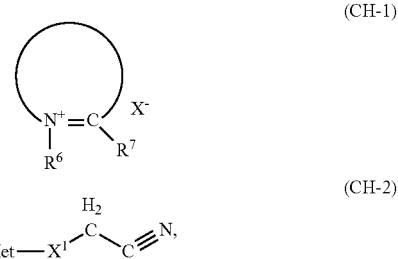

wherein:

$R^6$ represents a linear or cyclic ($C_1$ to $C_6$)alkyl group; a ($C_2$ to $C_6$)alkenyl group; an optionally substituted aryl group; an optionally substituted heteroaryl group; an aryl ($C_1$ to $C_6$)alkyl group; a ($C_1$ to $C_6$)hydroxyalkyl group; a ($C_2$ to $C_6$)polyhydroxyalkyl group; a ($C_1$ to $C_6$)alkoxy ($C_1$ to $C_6$)alkyl group; a group of the formula $R^I R^{II} N$—$(CH_2)_m$—, in which m is an integer of from 2 to 6, and $R^I$ and $R^{II}$ each independently of one another represent a hydrogen atom, a ($C_1$ to $C_4$)alkyl group, a ($C_1$ to $C_4$)hydroxyalkyl group, or an aryl-($C_1$ to $C_6$)alkyl group, it being possible for $R^I$ and $R^{II}$ together with the nitrogen atom to form a 5-, 6-, or 7-membered ring, $R^7$ represents a ($C_1$ to $C_6$)alkyl group, $X^-$ is a physiologically compatible anion, and the cycle of formula (CH-1) represents all ring structures which may additionally comprise further heteroatoms such as nitrogen, oxygen or sulfur and may further carry fused ring structures, all of which ring structures may carry additional substituents, Het represents an optionally substituted heteroaromatic group, and $X^1$ represents a covalent bond or a carbonyl group (C=O).

A process for multitonal dyeing of hair is also provided. The process comprises preparing an oxidative colorant agent (A); treating hair with the oxidative colorant agent (A) to give a colored hair; preparing a CH-acidic hair dyeing agent (B) having a pH of from about 7 to about 10, measured at 22° C.; treating the colored hair with the CH-acidic hair dyeing agent (B) to give a dyed hair; and treating the dyed hair with a cosmetic decolorizing agent (Ox) to give a multitonal dyed hair. The oxidative colorant agent (A) is prepared from at least a developer component, a coupler component, and an oxidizing agent. The CH-acidic hair dyeing agent (B) is prepared by mixing together: an agent (B1) comprising at least one reactive carbonyl compound in a cosmetic carrier, where the agent (B1) is free from CH-acidic compounds; an agent (B2) comprising at least one CH-acidic compound in a cosmetic carrier, where the agent (B2) is free from reactive carbonyl compounds; and an agent (B3) comprising at least one alkalizing agent. The agent (B2) comprises at least one CH-acidic compound selected from compounds of the formula (CH-1) and/or compounds of the formula (CH-2):

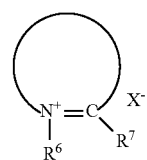

(CH-1)

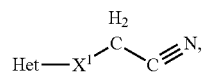

(CH-2)

wherein $R^6$ represents a substituted or unsubstituted linear or cyclic ($C_1$ to $C_6$)alkyl group, ($C_2$ to $C_6$)alkenyl group, aryl group, heteroaryl group, or aryl($C_1$ to $C_6$)alkyl group, or a group of the formula $R^I R^{II} N$—$(CH_2)_m$—, in which m is an integer of from 2 to 6, and $R^I$ and $R^{II}$ are each independently H, a ($C_1$ to $C_4$)alkyl group, a ($C_1$ to $C_4$)hydroxyalkyl group, or an aryl-($C_1$ to $C_6$)alkyl group, or $R^I$ and $R^{II}$ together represent a $C_3$ to $C_5$ alkylene group that together with the nitrogen atom form a 5-, 6-, or 7-membered ring; $R^7$ represents a ($C_1$ to $C_6$)alkyl group; $X^-$ is a physiologically compatible anion; Het represents an optionally substituted heteroaromatic group; and $X^1$ represents a covalent bond or a carbonyl group (C=O). The cosmetic decolorizing agent (Ox) has a pH value in the range from 4 to 11, measured at 22° C., and comprises water and from about 0.5 to about 12 wt. % hydrogen peroxide, based on the total weight of the decolorizing agent (Ox).

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Existing temporary colorants are often based on inorganic color pigments dispersed in a volatile carrier, usually with a high content of short-chain alcohols, and applied to the hair, in particular sprayed on. However, the color pigments usually adhere poorly to the hair and often trickle right off the hair after the carrier material dries or are quickly removed again by friction or combing. This is perceived as unpleasant by many consumers.

Accordingly, there is still a need for a coloring technique that allows oxidatively pre-colored and thus pre-damaged hair to be temporarily treated with a second hair color that also has good fastness properties but can be reliably removed completely after a short time without causing too much damage to the hair.

Another possibility for color change is the use of so-called CH-acid dyes. This is, similar to oxidative coloration, a reactive multicomponent system in which at least one compound having a reactive carbonyl group is reacted with at least one CH-acidic compound or with at least one compound having a primary or secondary amino group or hydroxy group selected from primary or secondary aromatic amines, nitrogen-comprising heterocyclic compounds, and aromatic hydroxy compounds. Both components are brought into contact with each other just before use; the dye-forming reaction is started by increasing the pH of the mixture.

The aforementioned components are generally not dyes themselves and are therefore not suitable by themselves for dyeing keratin-comprising fibers. In combination, they form dyes in a non-oxidative process called "CH-acid dyeing." On the keratin-comprising fiber, the resulting dyeings predominantly exhibit fastness properties comparable to those of oxidation dyeing. The range of shades that can be achieved with gentle CH-acid coloring is very broad, and the coloration obtained often exhibits high brilliance and color depth. Since CH-acid dyeing can achieve bright colors with good durability on the hair without the use of oxidizing agents such as hydrogen peroxide, this dyeing method is associated with significantly less damage to the hair and, against this background, is of particular interest to consumers. It is also interesting to note that the dyes developed on the hair during CH-acid dyeing can be completely removed by a short alkaline oxidation treatment without affecting the underlying oxidatively achieved hair color.

In the field of this application is based, it was surprisingly found that a process in which the hair is first oxidatively dyed (method step 1), then dyed with a colorant based on reactive carbonyl compounds and CH-acidic compounds (method step 2), and the CH-acidic dyeing is later decolorized again with an alkaline hydrogen peroxide-comprising composition (method step 3), solves the tasks set in an outstanding manner.

It is therefore an object of the present disclosure to provide a method for coloring hair in which in a first method step, the hair is treated with an oxidative colorant (A), in a subsequent, second step of the process, the hair is treated with a CH-acidic hair dyeing agent (B) which has a pH in the range from about 7 to about 10, measured at 22° C., and which is obtained immediately before use by mixing together the three agents (B1), (B2) and (B3) mentioned below:

an agent (B1) comprising in a cosmetic carrier at least one reactive carbonyl compound and being free from CH-acidic compounds, and an agent (B2) comprising, in a cosmetic carrier, at least one CH-acid compound selected from compounds of the formula (CH-1) and/or compounds of the formula (CH-2) and being free from reactive carbonyl compounds,

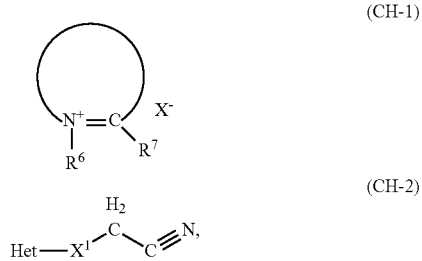

wherein
R$^6$ represents a linear or cyclic (C$_1$ to C$_6$) alkyl group, a (C$_2$ to C$_6$) alkenyl group, an optionally substituted aryl group, an optionally substituted heteroaryl group, an aryl (C$_1$ to C$_6$) alkyl group, a (C$_1$ to C$_6$) hydroxyalkyl group, a (C$_2$ to C$_6$) polyhydroxyalkyl group, a (C$_1$ to C$_6$) alkoxy (C$_1$ to C$_6$) alkyl group, a group R$^I$R$^{II}$N—(CH$_2$)$_m$—, in which R$^I$ and R$^{II}$ independently of one another represent a hydrogen atom, a (C$_1$ to C$_4$)-alkyl group, a (C$_1$ to C$_4$)-hydroxyalkyl group or an aryl-(C$_1$ to C$_6$)-alkyl group, it being possible for R$^I$ and R$^{II}$ together with the nitrogen atom to form a 5-, 6- or 7-membered ring, and m represents a number 2, 3, 4, 5 or 6, R$^7$ represents a (C$_1$ to C$_6$) alkyl group, in particular a methyl group X— stands for a physiologically compatible anion, the cycle of formula (CH-1) represents all ring structures which may additionally comprise further heteroatoms such as nitrogen, oxygen or sulfur and may further carry fused ring structures, all of which ring structures may carry additional substituents, Het represents an optionally substituted heteroaromatic compound, and X1 represents a direct bond or a carbonyl group, an agent (B3) comprising at least one alkalizing agent, subsequently, in a later, third method step, the hair is treated with a cosmetic decolorizing agent (Ox) which comprises water and further from about 0.5 to about 12% by weight, preferably from about 1 to about 6% by weight, more preferably from about 1 to about 4% by weight, very particularly preferably from about 1.5 to about 3% by weight, based in each case on the weight of the decolorizing agent (Ox), hydrogen peroxide and a pH in the range from about 4 to about 11, preferably in the range from about 5 to about 10.5, particularly preferably in the range from about 7 to about 10, in each case measured at 22° C., with a time interval in the range of 1 minute to 1.5 months between the individual method steps.

The method as contemplated herein comprises three steps. At each step of the method, a change in hair color is achieved. Each step of the process comprises several steps, including the preparation of the ready-to-use colorants immediately before application to the hair, the application of the dye or decolorizing agent to the hair and the exposure, rinsing the agents from the hair, if necessary, the application of a shampoo and/or a conditioner and finally, drying by letting it dry naturally or by using a hair dryer.

If the decolorizing agent applied in the third step of the method is to have a pH of about 5 or higher, it is useful to adjust the decolorizing agent to the desired pH immediately before its application to the hair by mixing an acidic aqueous hydrogen peroxide preparation with an alkalizing agent and then applying it to the hair immediately afterwards. This is necessary because aqueous hydrogen peroxide preparations can only be stored for a long time in strongly acidic conditions up to a maximum of approx. pH 5.5 or pH 5.

There is a time interval in the range of from about 1 minute to about 1.5 months between the individual process steps.

Between the oxidative hair dyeing in method step 1 and the CH-acid hair dyeing in method step 2 there is preferably a period of from about 30 minutes to about 1 month, particularly preferably from about 6 hours to about 14 days, exceptionally preferably from about 2 to about 10 days.

Between the CH-acid hair dyeing in method step 2 and the decolorization in method step 3 there is preferably a period of from about 30 minutes to about 14 days, particularly preferably from about 6 hours to about 3 days, exceptionally preferably from about 1 to about 2 days.

Method Step 1: Oxidative Coloring

In the method as contemplated herein, the hair is treated with an oxidative colorant (A) in a first method step.

The oxidative colorant (A) preferably comprises at least one oxidation dye precursor. As oxidation dye precursor, the agents (A) used in the method as contemplated herein preferably comprise at least one developer component.

As contemplated herein, it may be preferred to use a p-phenylenediamine derivative or one of its physiologically compatible salts as the developer component. Very particularly preferred p-phenylenediamine derivatives as contemplated herein are selected from at least one compound of the group p-phenylenediamine, p-toluenediamine, 2-(beta-hydroxyethyl)-p-phenylenediamine, 2-(alpha, beta-dihydroxyethyl)-p-phenylenediamine, N,N-bis-(beta-hydroxyethyl)-p-phenylenediamine, 2-methoxymethyl-p-phenylenediamine, N-(4-amino-3-methylphenyl)-N-[3-(1H-imidazol-1-yl)propyl]amine, and the physiologically tolerated salts of these compounds.

As contemplated herein, it may be further preferred to use as developer component compounds comprising at least two aromatic nuclei substituted with amino and/or hydroxyl groups. Very particularly preferred dinuclear developer components are selected from N,N'-bis-(beta-hydroxyethyl)-N,N'-bis-(4-aminophenyl)-1,3-diamino-propan-2-ol, bis-(2-hydroxy-5-aminophenyl)-methane, 1,3-bis-(2,5-diaminophenoxy)-propan-2-ol, N,N'-bis-(4-aminophenyl)-1,4-diazacycloheptane, 1,10-bis-(2,5-diaminophenyl)-1,4,7,10-tetraoxadecane or one of the physiologically tolerated salts of these compounds.

Furthermore, it may be preferred as contemplated herein to use a p-aminophenol derivative or one of its physiologically acceptable salts as the developer component. Very particularly preferred compounds are p-aminophenol, 4-amino-3-methylphenol, 4-amino-2-aminomethylphenol, 4-amino-2-(alpha, beta-dihydroxyethyl)phenol and 4-amino-2-(diethylaminomethyl)phenol.

Further, the developer component may be selected from o-aminophenol and its derivatives, such as 2-amino-4-methylphenol, 2-amino-5-methylphenol, or 2-amino-4-chlorophenol. Furthermore, the developer component may be selected from heterocyclic developer components, such as pyrimidine derivatives, pyrazole derivatives, pyrazolopyrimidine derivatives or their physiologically acceptable salts.

Particularly preferred pyrimidine derivatives are especially the compounds 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine.

Particularly preferred pyrazole derivatives are especially the compounds selected from 4,5-diamino-1-methylpyrazole, 4,5-diamino-1-(beta-hydroxyethyl)-pyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert.-butyl-1-methylpyrazole, 4,5-diamino-1-tertbutyl-3-methylpyrazole, 4,5-diamino-1-(beta-hydroxyethyl)-3-methylpyrazole, 4,5-diamino-1-ethyl-3-methylpyrazole, 4,5-diamino-1-ethyl-3-(4'-methoxyphenyl)-pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(beta-aminoethyl)amino-1,3-dimethylpyrazole, and their physiologically tolerated salts. Very particularly preferred developer components are selected from at least one compound selected from the group of p-phenylenediamine, p-toluylenediamine, 2-(beta-hydroxyethyl)-p-phenylenediamine, 2-methoxymethyl-p-phenylenediamine, 2-(alpha, beta-dihydroxyethyl)-p-phenylenediamine, N,N-bis-(beta-hydroxyethyl)-p-phenylenediamine, N-(4-amino-3-methylphenyl)-N-[3-(1H-imidazol-1-yl)propyl]amine, N,N'-bis-(beta-hydroxyethyl)-N,N'-bis-(4-aminophenyl)-1,3-diamino-propan-2-ol, bis-(2-hydroxy-5-aminophenyl)methane, 1,3-bis-(2,5-diaminophenoxy)-propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(alpha, beta-dihydroxyethyl)-phenol, and 4-amino-2-(diethylaminomethyl)-phenol, 4,5-diamino-1-(beta-hydroxyethyl)-pyrazole, 2,4,5,6-tetraaminopyrimidine, 4-hydroxy-2,5,6-triaminopyrimidine, 2-hydroxy-4,5,6-triaminopyrimidine, and the physiologically tolerated salts of these compounds and mixtures of these compounds and their salts.

The at least one developer component is preferably present in a total amount of from about 0.001 to about 10% by weight, particularly preferably from about 0.3 to about 5% by weight, exceptionally preferably 0.7 to about 3% by weight, in each case based on the ready-to-use colorant (A) as contemplated herein.

The agents (A) used in the method as contemplated herein may comprise at least one coupler component in addition to the developer component.

Coupler components do not form significant coloration on their own during oxidative coloring, but always require the presence of developer components. Therefore, as contemplated herein, it is preferred that when at least one developer component is used, at least one coupler component is also used.

Coupler components as contemplated herein allow at least one substitution of a chemical residue of the coupler by the oxidized form of the developer component. In this method, a covalent bond is formed between the coupler and developer components. Couplers are preferably cyclic compounds carrying on the cycle at least two groups selected from
(i) optionally substituted amino groups and/or
(ii) hydroxy groups.

If the cyclic compound is a six-membered ring (preferably aromatic), said groups are preferably in ortho-position or meta-position to each other.

Coupler components as contemplated herein are preferably selected as at least one compound from one of the following classes:
  m-Aminophenol and/or derivatives thereof,
  m-diaminobenzene and/or derivatives thereof,
  o-Diaminobenzene and/or its derivatives,
  o-aminophenol derivatives, such as o-aminophenol,
  Naphthalene derivatives having at least one hydroxy group,
  Di- or trihydroxybenzene, respectively, and/or derivatives thereof,
  Pyridine derivatives,
  Pyrimidine derivatives,
  Monohydroxyindole derivatives and/or monoaminoindole derivatives,
  Monohydroxyindoline derivatives and/or monoaminoindoline derivatives,
  Pyrazolone derivatives, such as 1-phenyl-3-methylpyrazol-5-one,
  Morpholine derivatives such as 6-hydroxybenzomorpholine or 6-amino-benzomorpholine,
  Quinoxaline derivatives such as 6-methyl-1,2,3,4-tetrahydroquinoxaline,
  Mixtures of two or more compounds from one or more of these classes are also as contemplated herein in the context of this embodiment.

Particularly preferred m-aminophenol coupling components are selected from at least one compound selected from the group of m-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)-amino-2-methylphenol, 3-(diethylamino)-phenol, N-cyclopentyl-3-aminophenol, 1,3-dihydroxy-5-(methylamino)-benzene, 3-ethylamino-4-methylphenol, 2,4-dichloro-3-aminophenol and the physiologically tolerated salts of all the above compounds. Particularly preferred m-diaminobenzene coupler components are selected from at least one compound selected from the group formed from m-phenylenediamine, diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-yl)phenyl)amino]ethanol, 3-amino-4-(2-methoxyethoxy)-5-methylphenylamine, 1-amino-3-bis(2'-hydroxyethyl)-aminobenzene and the physiologically tolerated salts of all the above compounds.

Particularly preferred o-diaminobenzene coupling components are selected from at least one compound selected from the group of 3,4-diaminobenzoic acid and 2,3-diamino-1-methylbenzene and the physiologically acceptable salts of all the above compounds.

Preferred di- or trihydroxybenzenes and derivatives thereof are selected from at least one compound of the group formed by resorcinol, resorcinol monomethyl ether, 2-methyl resorcinol, 5-methyl resorcinol, 2,5-dimethyl resorcinol, 2-chloro resorcinol, 4-chloro resorcinol, pyrogallol and 1,2,4-trihydroxybenzene.

Particularly preferred pyridine derivatives are selected from at least one compound of the group formed by 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine, and the physiologically tolerated salts of the abovementioned compounds.

Preferred naphthalene derivatives having at least one hydroxy group are selected from at least one compound of the group formed by 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene.

Particularly preferred indole derivatives are selected from at least one compound of the group formed by 4-hydroxyindole, 6-hydroxyindole and 7-hydroxyindole and the physiologically tolerable salts of the aforementioned compounds.

Particularly preferred indoline derivatives are selected from at least one compound of the group formed by 4-hydroxyindoline, 6-hydroxyindoline and 7-hydroxyindoline and the physiologically tolerable salts of the aforementioned compounds.

Preferred pyrimidine derivatives are selected from at least one compound of the group formed from 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine and the physiologically tolerated salts of the aforementioned compounds.

Particularly preferred coupler components as contemplated herein are selected from m-aminophenol, 5-amino-2-methylphenol, 3-amino-2-chloro-6-methylphenol, 2-hydroxy-4-aminophenoxyethanol, 5-amino-4-chloro-2-methylphenol, 5-(2'-hydroxyethyl)amino-2-methylphenol, 2,4-dichloro-3-aminophenol, o-aminophenol, m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis(2'-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically tolerated salts of the abovementioned compounds.

The at least one coupler component is preferably present in a total amount of from about 0.001 to about 10% by weight, particularly preferably from about 0.3 to about 5% by weight, exceptionally preferably from about 0.7 to about 3% by weight, in each case based on the ready-to-use colorant (A) as contemplated herein.

Developer components and coupler components are generally used in approximately equimolar amounts to each other. Although equimolar use has been shown to be appropriate, a certain excess of individual oxidation dye precursors is not detrimental, so that developer components and coupler components can be in a molar ratio of from about 1:0.5 to about 1:3, especially from about 1:1 to about 1:2.

As contemplated herein, it may be preferable to add a natural analogous dye as a further dye precursor to the agent (A) of the method as contemplated herein.

Preferred dye precursors for natural analog dyes are indoles and indolines comprising at least two groups selected from hydroxy and/or amino groups, preferably as substituent on the six-membered ring. These groups may carry further substituents, e.g. in the form of etherification or esterification of the hydroxy group or alkylation of the amino group. In a further embodiment, the colorants comprise at least one indole and/or indoline derivative. Compositions as contemplated herein comprising precursors of natural analogous dyes are preferably used as air oxidative colorants. Consequently, in this embodiment, no additional oxidizing agent is added to said compositions.

Derivatives of 5,6-dihydroxyindoline are particularly well suited as precursors of natural analog hair dyes. Particularly noteworthy within this group are N-methyl-5,6-dihydroxyindoline, N-ethyl-5,6-dihydroxyindoline, N-propyl-5,6-dihydroxyindoline, N-butyl-5,6-dihydroxyindoline, and especially the 5,6-dihydroxyindoline.

Furthermore, derivatives of 5,6-dihydroxyindole are excellently suited as precursors of natural analog hair dyes. Within this group, N-methyl-5,6-dihydroxyindole, N-ethyl-5,6-dihydroxyindole, N-propyl-5,6-dihydroxyindole, N-butyl-5,6-dihydroxyindole and, in particular, 5,6-dihydroxyindole should be highlighted.

The indoline or indole derivatives can be used both as free bases and in the form of their physiologically compatible salts with inorganic or organic acids, e.g. hydrochlorides, sulfates and hydrobromides.

Furthermore, the agent (A) may additionally comprise at least one direct dye. These are dyes that are absorbed directly onto the hair and do not require an oxidative method to form the color. Direct dyes are usually nitrophenylenediamines, nitroaminophenols, azo dyes, anthraquinones or indophenols.

The direct dyes are each preferably used in an amount of from about 0.001 to about 20% by weight, based on the total application preparation. The total amount of direct dyes is preferably not more than about 20% by weight.

Direct dyes can be divided into anionic, cationic and nonionic direct dyes.

Preferred anionic direct dyes are the compounds known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

Preferred cationic direct dyes in this context are
(a) cationic triphenylmethane dyes, such as Basic Blue 7, Basic Blue 26, Basic Violet 2 and Basic Violet 14,
(b) aromatic systems substituted with a quaternary nitrogen group, such as Basic Yellow 57, Basic Red 76, Basic Blue 99, Basic Brown 16 or Basic Brown 17, and
(c) direct-drawing dyes comprising a heterocycle having at least one quaternary nitrogen atom, such as those recited in EP-A2-998 908, explicitly referred to herein, in claims 6 to 11. The dyes known under the names Basic Yellow 87, Basic Orange 31 and Basic Red 51 are particularly preferred cationic direct dyes of group (c).

As contemplated herein, the cationic direct dyes sold under the trade name Arianor® are also very particularly preferred cationic direct dyes.

Preferred nonionic direct dyes are those known under the international designations or trade names of HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid, and 2-chloro-6-ethylamino-4-nitrophenol.

Furthermore, naturally occurring dyes such as those found in henna red, henna neutral, henna black, chamomile flower, sandalwood, black tea, sloth bark, sage, blue wood, madder root, catechu, sedre and alcanna root can also be used as direct dyes.

Furthermore, the agent (A) as contemplated herein may also comprise naturally occurring dyes, such as those found in henna red, henna neutral, henna black, chamomile flower, sandalwood, black tea, sloth bark, sage, blue wood, madder root, catechu, sedre and alcanna root.

The actual oxidative coloring of the hair can in principle be carried out with atmospheric oxygen, atmospheric oxygen not being a chemical oxidant within the meaning of the present application. Preferably, however, a chemical oxidizing agent is used, especially when a lightening effect on human hair is desired in addition to coloring. In a preferred embodiment of this subject matter of the present disclosure, therefore, the agent (A) is prepared immediately before use from an agent (A1) comprising an oxidation dye precursor and an agent (A2) comprising an oxidizing agent.

Suitable oxidizing agents are persulfates, chlorites and, in particular, hydrogen peroxide or its addition products to urea, melamine and sodium borate. As contemplated herein, however, the oxidation colorant can also be applied to the hair together with a catalyst which activates the oxidation of the dye precursors, e.g. by atmospheric oxygen. Such catalysts include metal ions, iodides, quinones, or certain enzymes. As contemplated herein, it is preferred that the agent (A2) comprises hydrogen peroxide as oxidizing agent.

The actual oxidative hair colorant is conveniently prepared immediately before use by mixing the preparation of the oxidizing agent (A2) with the preparation (A1) comprising the dye precursors. The resulting ready-to-use oxidative hair colorant (A) preferably has a pH in the range from about 6 to about 12, particularly preferably in the range from about 8 to about 10.5, exceptionally preferably in the range from about 9 to about 10, in each case measured at 22° C. The application temperatures can be in a range between about 15 and about 40° C. After an exposure time of about 5 to about 45 minutes, the hair dye is removed from the hair to be dyed by rinsing. There is no need to rewash with a shampoo if a carrier with a high surfactant content, e.g. a dyeing shampoo, has been used.

However, especially in the case of hair that is difficult to dye, the preparation with the dye precursors can also be applied to the hair without prior mixing with the oxidation component. After an exposure time of from about 20 to about 30 minutes, the oxidation component is then applied—if necessary after an intermediate rinse. After a further exposure time of about from 10 to about 20 minutes, rinse and, if desired, re-shampoo. In this embodiment, according to a first variant in which the prior application of the dye precursors is intended to improve penetration into the hair, the corresponding agent is adjusted to a pH of from about 4 to about 7. According to a second variant, air oxidation is initially sought, with the applied agent preferably having a pH of from about 7 to about 10. In the subsequent accelerated post-oxidation, the use of acid-adjusted peroxodisulfate solutions as oxidizing agents may be preferred.

Method Step 2: CH-Acid Coloring

In the second step of the method as contemplated herein, the hair is treated with an agent (B) which has a pH in the range from about 7 to about 10, measured at 22° C., and which, immediately before application, is composed of an agent (B1) comprising at least one reactive carbonyl compound an agent (B2) comprising at least one CH-acid compound selected from compounds of formula (CH-1) and/or compounds of formula (CH-2), and an agent (B3) comprising at least one alkalizing agent, by mixing agents (B1), (B2) and (B3) together.

Compound (B) preferably has a pH in the range from about 8 to about 9.5, particularly preferably in the range from about 8.5 to about 9, in each case measured at 22° C.

The agent (B1) comprises at least one reactive carbonyl compound and is free from CH-acidic compounds.

Reactive carbonyl compounds as contemplated herein have at least one carbonyl group as a reactive group, which reacts with the CH-acidic component to form a covalent bond. Preferred reactive carbonyl compounds are selected from compounds bearing at least one formyl group and/or at least one keto group, in particular at least one formyl group.

Furthermore, as contemplated herein, compounds can also be used as reactive carbonyl compounds in agent (B1) in which the reactive carbonyl group is derivatized or masked in such a way that the reactivity of the carbon atom of the derivatized carbonyl group towards the CH-acidic component is always present. These derivatives are preferably addition compounds a) of amines and their derivatives to form imines or oximes as addition compounds b) of alcohols with formation of acetals or ketals as addition compound c) of water to form hydrates as an addition compound (the reactive carbonyl compound is derived from an aldehyde in this case c))

to the carbon atom of the carbonyl group of the reactive carbonyl compound.

Among the reactive carbonyl compounds, the following compounds are preferred: Benzaldehyde and its derivatives, naphthaldehyde and its derivatives, cinnamaldehyde and its derivatives, 2-formylmethylene-1,3,3-trimethylindoline (Fischer's aldehyde or tribase aldehyde), 2-indole aldehyde, 3-indole aldehyde, 1-methylindole-3-aldehyde, 2-methylindole-3-aldehyde, 2-(1',3',3'-trimethyl-2-indolinydene)-acetaldehyde, 1-methylpyrrole-2-aldehyde, pyridoxal, 2,3-dihydro-1,5-dimethyl-3-oxo-2-phenyl-1H-pyrazole-4-carboxaldehyde, Furfural, 5-nitrofurfural, chromone-3-aldehyde, 3-(5'-nitro-2'-furyl)-acrolein, 3-(2'-furyl)-acrolein and imidazole-2-aldehyde, 5-(4-dimethylaminophenyl)penta-2,4-dienal, 5-(4-diethylaminophenyl)penta-2,4-dienal, 5-(4-methoxyphenyl)penta-2,4-dienal, 5-(3,4-dimethoxyphenyl)penta-2,4-dienal, 5-(2,4-dimethoxyphenyl)penta-2,4-dienal, 5-(4-piperidinophenyl)penta-2,4-dienal, 5-(4-morpholinophenyl)penta-2,4-dienal, 5-(4-pyrrolidinophenyl)penta-2,4-dienal, 5-(4-dimethylamino-1-naphthyl)penta-3,5-dienal, piperonal, 6-nitropiperonal, 2-nitropiperonal, 5-nitrovanillin, 2,5-dinitrosalicylaldehyde, 5-bromo-3-nitrosalicylaldehyde, 3-nitro-4-formylbenzenesulfonic acid, 4-formyl-1-methylpyridinium-, 2-formyl-1-methylpyridinium-, 4-formyl-1-ethylpyridinium-, 2-formyl-1-ethylpyridinium-, 4-formyl-1-benzylpyridinium-, 2-formyl-1-benzylpyridinium-, 4-formyl-1,2-dimethylpyridinium-, 4-formyl-1,3-dimethylpyridinium-, 4-formyl-1-methylquinolinium-, 2-formyl-1-methylquinolinium-, 5-formyl-1-methylquinolinium-, 6-formyl-1-methylquinolinium-, 7-formyl-1-methylquinolinium-, 8-formyl-1-methylquinolinium, 5-formyl-1-ethylquinolinium-, 6-formyl-1-ethylquinolinium-, 7-formyl-1-ethylquinolinium-, 8-formyl-1-ethylquinolinium, 5-formyl-1-benzylquinolinium-, 6-formyl-1-benzylquinolinium-, 7-formyl-1-benzylquinolinium-, 8-formyl-1-benzylquinolinium, 5-formyl-1-allylquinolinium-, 6-formyl-1-allylquinolinium-, 7-formyl-1-allylquinolinium- and 8-formyl-1-allylquinolinium-benzenesulfonate, -p-toluenesulfonate, -methanesulfonate, -perchlorate, -sulfate, -chloride, -bromide, -iodide, -tetrachlorozincate, -methyl sulfate-, -trifluoromethanesulfonate, -tetrafluoroborate, isatin, 1-methyl-isatin, 1-allyl-isatin, 1-hydroxymethyl-isatin, 5-chloro-isatin, 5-methoxy-isatin, 5-nitro-isatin, 6-nitro-isatin, 5-sulfo-isatin, 5-carboxy-isatin, quinisatin, 1-methylquinisatin, and any mixtures of the foregoing compounds.

In particular, it is preferred that at least one compound selected from 4-hydroxy-3-methoxybenzaldehyde, 3,5-dimethoxy-4-hydroxybenzaldehyde, 4-hydroxy-1-naphthaldehyde, 4-hydroxy-2-methoxybenzaldehyde, 3,4-dihydroxy-5-methoxybenzaldehyde, 3,4,5-trihydroxybenzaldehyde, 3,5-dibromo-4-hydroxybenzaldehyde, 4-hydroxy-3-nitrobenzaldehyde, 3-bromo-4-hydroxybenzaldehyde, 4-hydroxy-3-methylbenzaldehyde, 3,5-dimethyl-4-hydroxybenzaldehyde, 5-bromo-4-hydroxy-3-methoxybenzaldehyde, 4-diethylamino-2-hydroxybenzaldehyde, 4-dimethylamino-2-methoxybenzaldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxy-benzaldehyde, 4-hydroxy-2,5-dimethoxy-benzaldehyde, 4-hydroxy-2,6-dimethoxy-benzaldehyde, 4-hydroxy-2-methyl-benzaldehyde, 4-hydroxy-2,3-dimethyl-benzaldehyde, 4-hydroxy-2,5-dimethyl-benzaldehyde, 4-hydroxy-2,6-dimethyl-benzaldehyde, 3,5-diethoxy-4-hydroxy-benzaldehyde, 2,6-diethoxy-4-hydroxy-benzaldehyde, 3-hydroxy-4-methoxy-benzaldehyde, 2-hydroxy-4-methoxy-benzaldehyde, 2-ethoxy-4-hydroxy-benzaldehyde, 3-ethoxy-4-hydroxy-benzaldehyde, 4-ethoxy-2-hydroxy-benzaldehyde, 4-ethoxy-3-hydroxy-benzaldehyde, 2,3-dimethoxybenzaldehyde, 2,4-dimethoxybenzaldehyde, 2,5-dimethoxybenzaldehyde, 2,6-dimethoxybenzaldehyde, 3,4-dimethoxybenzaldehyde, 3,5-dimethoxybenzaldehyde, 2,3,4-trimethoxybenzaldehyde, 2,3,5-trimethoxybenzaldehyde, 2,3,6-trimethoxybenzaldehyde, 2,4,6-trimethoxybenzaldehyde, 2-hydroxybenzaldehyde, 3-hydroxybenzaldehyde, 4-hydroxybenzaldehyde, 2,3-dihydroxybenzaldehyde, 2,4-dihydroxybenzaldehyde, 2,4-dihydroxy-3-methyl-benzaldehyde, 2,4-dihydroxy-5-methyl-benzaldehyde, 2,4-dihydroxy-6-methyl-benzaldehyde, 2,4-dihydroxy-3-methoxy-benzaldehyde, 2,4-dihydroxy-5-methoxy-benzaldehyde, 2,4-dihydroxy-6-methoxy-benzaldehyde, 2,5-dihydroxybenzaldehyde, 2,6-dihydroxybenzaldehyde, 3,4-dihydroxybenzaldehyde, 3,4-dihydroxy-2-methyl-benzaldehyde, 3,4-dihydroxy-5-methyl-benzaldehyde, 3,4-dihydroxy-6-methyl-benzaldehyde, 3,4-dihydroxy-2-methoxy-benzaldehyde, 3,5-dihydroxybenzaldehyde, 2,3,4-trihydroxybenzaldehyde, 2,3,5-trihydroxybenzaldehyde, 2,3,6-trihydroxybenzaldehyde, 2,4,6-trihydroxybenzaldehyde, 2,4,5-trihydroxybenzaldehyde, 2,5,6-trihydroxybenzaldehyde, 4-dimethylaminobenzaldehyde, 4-diethylaminobenzaldehyde, 4-dimethylamino-2-hydroxybenzaldehyde, 4-pyrrolidinobenzaldehyde, 4-morpholinobenzaldehyde, 2-morpholinobenzaldehyde, 4-piperidinobenzaldehyde, 3,5-dichloro-4-hydroxybenzaldehyde, 4-hydroxy-3,5-diiodo-benzaldehyde, 3-chloro-4-hydroxybenzaldehyde, 5-chloro-3,4-dihydroxybenzaldehyde, 5-bromo-3,4-dihydroxybenzaldehyde, 3-chloro-4-hydroxy-5-methoxybenzaldehyde, 4-hydroxy-3-iodo-5-methoxybenzaldehyde, 2-methoxy-1-naphthaldehyde, 4-methoxy-1-naphthaldehyde, 2-hydroxy-1-naphthaldehyde, 2,4-dihydroxy-1-napthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-dimethylamino-1-naphthaldehyde, 3-hydroxy-4-nitrobenzaldehyde, 2-hydroxy-3-methoxy-5-nitrobenzaldehyde, 5-nitrovanillin, 2,5-dinitrosalicylaldehyde, 5-bromo-3-nitrosalicylaldehyde, 2-dimethylaminobenzaldehyde, 2-chloro-4-dimethylaminobenzaldehyde, 4-dimethylamino-2-methylbenzaldehyde, 4-diethylamino-cinnamaldehyde, 4-dibutylamino-benzaldehyde, 3-carboxy-4-hydroxybenzaldehyde, 5-carboxyvanillin, 3-carboxy-4-hydroxy-5-methylbenzaldehyde, 3-carboxy-5-ethoxy-4-hydroxybenzaldehyde, 3-carboxy-4-hydroxybenzaldehyde, 5-carboxyvanillin, 3-carboxy-4-hydroxy-5-methylbenzaldehyde, 3-carboxy-5-ethoxy-4-hydroxybenzaldehyde, 3-Allyl-4-hydroxybenzaldehyde, 3-Allyl-4-hydroxy-5-methoxybenzaldehyde, 3-Allyl-4-hydroxy-5-methylbenzaldehyde, 3-Allyl-5-bromo-4-hydroxybenzaldehyde, 3,5-diallyl-4-hydroxybenzaldehyde, 3-Allyl-5-carboxy-4-hydroxybenzaldehyde (3-Allyl-5-formyl-2-hydroxybenzoic acid), 3-allyl-4-hydroxy-5-formylbenzaldehyde, 5-allyl-4-hydroxyisophthalaldehyde, 2,3-dihydro-1,5-dimethyl-3-oxo-2-phenyl-1H-pyrazole-4-carboxaldehyde and 4-formyl-1-methylquinolinium-p-toluenesulfonate and any mixtures of the foregoing compounds.

In a preferred embodiment of the method as contemplated herein, the agent (B1) comprises at least one reactive carbonyl compound selected from 4-hydroxy-2-methoxybenzaldehyde, 2-chloro-3,4-dihydroxybenzaldehyde, 2-bromo-3,4-dihydroxybenzaldehyde, 3,4-dihydroxy-5-methoxybenzaldehyde, 2,3-dihydro-1,5-dimethyl-3-oxo-2-phenyl-1H-pyrazole-4-carboxaldehyde, 2,4-dimethoxybenzaldehyde and 4-formyl-1-methylquinolinium-p-toluenesulfonate, and mixtures thereof.

Agents (B1) which comprise 4-formyl-1-methylquinolinium-p-toluenesulfonate in combination with at least one further reactive carbonyl compound selected from 3,4-dihydroxy-5-methoxybenzaldehyde, 2-chloro-3,4-dihydroxybenzaldehyde, 2-bromo-3,4-dihydroxybenzaldehyde, 3,4-dihydroxy-5-methoxybenzaldehyde, 2,3-dihydro-1,5-dimethyl-3-oxo-2-phenyl-1H-pyrazole-4-carboxaldehyde and 2,4-dimethoxy-benzaldehyde.

The reactive carbonyl compound(s) of the agent (B1) are preferably present in an amount of from about 0.03 to about 65.00 mmol, based on 100 g of the agent (B1). A content of from about 1.00 to about 30.00 mmol, based on 100 g of the agent (B1), is particularly preferred.

For the storage stability of the reactive carbonyl compounds, it is preferred that the agent (B1) has a pH in the range of from about 2 to about 5, preferably from about 3 to about 4, in each case measured at 22° C.

The agent (B2) comprises at least one CH-acid compound of the general formula (CH-1) and/or the general formula (CH-2) (vide supra) and is free from reactive carbonyl compounds.

CH-acid compounds are generally considered to be those compounds which carry a hydrogen atom bonded to an aliphatic carbon atom, whereby an activation of the corresponding carbon-hydrogen bond is effected due to electron-withdrawing substituents. The compounds according to formula (CH-1) and (CH-2) are CH-acidic compounds. From the cationic compounds of formula (CH-1), the corresponding uncharged enamine form can be specifically prepared by the addition of a base which causes the elimination of a proton. As an example for compounds according to formula (CH-1), the representation of the enamine form is illustrated below using the formulas (CH-1-A) and (CH-1-B) with $R^7$=$CH_3$. The corresponding enamine forms of the CH-acidic compounds according to formula (CH-1) are also as contemplated herein.

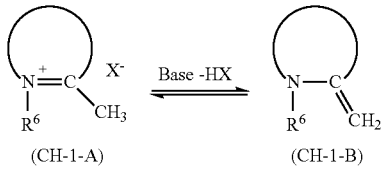

(CH-1-A)    (CH-1-B)

As contemplated herein, it is particularly preferred to select the compounds of formula (CH-1) from at least one compound of formula (CH-3),

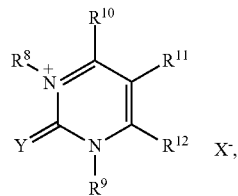

(CH-3)

wherein $R^8$ and $R^9$ independently represent a linear or cyclic ($C_1$ to $C_6$)alkyl group, a ($C_2$ to $C_6$)alkenyl group, an optionally substituted aryl group, an optionally substituted heteroaryl group, an aryl ($C_1$ to $C_6$)alkyl group, a ($c_1$ to $c_6$)hydroxyalkyl group, a ($C_2$ to $C_6$)polyhydroxyalkyl group, a ($C_1$ to $C_6$)alkoxy ($C_1$ to $C_6$)alkyl group, a group $R^I R^{II} N$—$(CH_2)_m$—, wherein $R^I$ and $R^{II}$ independently represent a hydrogen atom, a ($C_1$ to $C_4$)alkyl group, a ($C_1$ to C4)hydroxyalkyl group or an aryl-($C_1$ to $C_4$)alkyl group, wherein $R^I$ and $R^{II}$ together with the nitrogen atom may form a 5-, 6- or 7-membered ring and m represents a number 2, 3, 4,5 or 6, $R^{10}$ and $R^{12}$ independently represent a hydrogen atom or a $C_1$-$C_6$ alkyl group, at least one of $R^{10}$ and $R^{12}$ being a ($C_1$ to $C_6$)alkyl group, $R^{11}$ represents a hydrogen atom, a ($C_1$ to $C_6$)-alkyl group, a ($C_1$ to $C_6$)-hydroxyalkyl group, a ($C_2$ to $C_6$)-polyhydroxyalkyl group, a ($C_1$ to $C_6$)-alkoxy group, a ($C_1$ to $C_6$)-hydroxyalkoxy group, a group $R^{III} R^{IV} N$—$(CH_2)_q$—, wherein $R^{III}$ and $R^{IV}$ independently represent a hydrogen atom, a ($C_1$ to $C_6$) alkyl group, a ($C_1$ to $C_6$) hydroxyalkyl group or an aryl-($C_1$ to $C_6$) alkyl group and q represents a number 1, 2, 3, 4,5 or 6, it being possible for the radical R11 to form, together with one of the radicals $R^{10}$ or $R^{12}$, a 5-membered or 6-membered aromatic ring optionally comprising a halogen atom, a ($C_1$ to $C_6$) alkyl group, a ($C_1$ to $C_6$) hydroxyalkyl group, a ($C_2$ to $C_6$) polyhydroxyalkyl group, a ($C_1$ to $C_6$) alkoxy group, a ($c_1$ to $c_6$) hydroxyalkoxy group, a nitro group, a hydroxy group, a group $R^V R^{VI} N$—$(CH_2)_s$—, in which $R^V$ and $R^{VI}$ independently of one another represent a hydrogen atom, a ($C_1$ to $C_6$)-alkyl group, a ($C_1$ to $C_6$)-hydroxyalkyl group or an aryl-($C_1$ to $C_6$)-alkyl group and s represents a number 0, 1, 2, 3, 4,5 or 6, Y represents an oxygen atom, a sulfur atom or a group $NR^{VII}$, wherein $R^{VII}$ represents a hydrogen atom, an aryl group, a heteroaryl group, a ($C_1$ to $C_6$) alkyl group or an aryl ($C_1$ to $C_6$) alkyl group, and X— stands for a physiologically compatible anion.

At least one group $R^{10}$ or $R^{12}$ according to formula (CH-3) necessarily represents a ($C_1$ to $C_6$)-alkyl group. This alkyl group preferably carries at least two hydrogen atoms on its alpha carbon atom. Particularly preferred alkyl groups are methyl, ethyl, propyl, n-butyl, iso-butyl, n-pentyl, neopentyl, n-hexyl. Most preferably, $R^{10}$ and $R^{12}$ independently represent hydrogen or a methyl group, with at least one $R^{10}$ or $R^{12}$ group representing a methyl group.

In a preferred embodiment, Y of formula (CH-3) represents an oxygen atom or a sulfur atom, particularly preferably an oxygen atom.

The radical $R^8$ of formula (CH-3) is preferably selected from a ($C_1$ to $C_6$) alkyl group, particularly preferably a methyl group, a ($C_2$ to $C_6$) alkenyl group, particularly an allyl group, a ($C_2$ to $C_6$) hydroxyalkyl group, particularly a 2-hydroxyethyl group, or an optionally substituted benzyl group.

$R^{11}$ of the formula (CH-3) preferably represents a hydrogen atom.

Particularly preferably, in formula (CH-3), the radicals $R^9$, $R^{10}$ and $R^{12}$ represent a methyl group, the radical $R^{11}$ represents a hydrogen atom, Y represents an oxygen or a sulfur atom, and the radical $R^8$ is selected from a ($C_1$ to $C_6$)alkyl group, particularly preferably a methyl group, a ($C_2$ to $C_6$)alkenyl group, in particular an allyl group, a ($C_2$ to $C_6$)hydroxyalkyl group, in particular a 2-hydroxyethyl group, or an optionally substituted benzyl group.

Preferably, the at least one CH-acidic compound of formula (CH-1) and/or formula (CH-2) is selected from at least one compound of the group 2-(2-furoyl)-acetonitrile, 2-(5-bromo-2-furoyl)-acetonitrile, 3-(2,5-dimethyl-3-furyl)-3-oxopropanitrile, 2-(2-thenoyl)-acetonitrile, 2-(3-thenoyl)-acetonitrile, 2-(5-fluoro-2-thenoyl)-acetonitrile, 2-(5-chloro-2-thenoyl)-acetonitrile, 2-(5-bromo-2-thenoyl)-acetonitrile, 2-(5-methyl-2-thenoyl)-acetonitrile, 2-(2,5-dimethylpyrrole-3-oyl)-acetonitrile, 2-(1,2,5-trimethylpyrrole-3-oyl)-acetonitrile, 1H-benzimidazole-2-ylacetonitrile (also known as 2-(cyanmethyl)-benzimidazole), 1H-benzothiazole-2-ylacetonitrile, 2-(pyrid-2-yl)-acetonitrile, 2,6-bis(cyanmethyl)-pyridine, 2-(indole-3-oyl)-acetonitrile, 2-(2-methyl-indole-3-oyl)-acetonitrile, 2-(6-hydroxy-4,7-dimethoxy-1-benzofuran-5-oyl)-acetonitrile and the salts with physiologically tolerated counterion X— of 1,2-dihydro-1,3,4,6-tetramethyl-2-oxo-pyrimidinium, 1,2-dihydro-1,3-diethyl-4,6-dimethyl-2-oxo-pyrimidinium, 1,2-dihydro-1,3-dipropyl-4,6-dimethyl-2-oxo-pyrimidinium, 1,2-dihydro-1,3-di(2-hydroxyethyl)-4,6-dimethyl-2-oxo-pyrimidinium, 1,2-dihydro-1,3-diphenyl-4,6-dimethyl-2-oxo-pyrimidinium, 1,2-dihydro-1,3,4-trimethyl-2-oxo-pyrimidinium, 1,2-dihydro-1,3-diethyl-4-methyl-2-oxo-pyrimidinium, 1,2-dihydro-1,3-dipropyl-4-methyl-2-oxo-pyrimidinium, 1,2-dihydro-1,3-di(2-hydroxyethyl)-4-methyl-2-oxo-pyrimidinium, 1,2-dihydro-1,3-diphenyl-4-methyl-2-oxo-pyrimidinium, 1-allyl-1,2-dihydro-3,4,6-trimethyl-2-oxo-pyrimidinium, 1,2-dihydro-1-(2-hydroxyethyl)-3,4,6-trimethyl-2-oxo-pyrimidinium, 1,2-dihydro-1,3,4,6-tetramethyl-2-thioxo-pyrimidinium, 1,2-dihydro-1,3-diethyl-4,6-dimethyl-2-thioxo-pyrimidinium, 1,2-dihydro-1,3-dipropyl-4,6-dimethyl-2-thioxo-pyrimidinium, 1,2-dihydro-1,3-di(2-hydroxyethyl)-4,6-dimethyl-2-thioxo-pyrimidinium, 1,2-dihydro-1,3-diphenyl-4,6-dimethyl-2-thioxo-pyrimidinium, 1,2-dihydro-1,3,4-trimethyl-2-thioxo-pyrimidinium, 1,2-dihydro-1,3-diethyl-4-methyl-2-thioxo-pyrimidinium, 1,2-dihydro-1,3-dipropyl-4-methyl-2-thioxo-pyrimidinium, 1,2-dihydro-1,3-di(2-hydroxyethyl)-4-methyl-2-thioxo-pyrimidinium, 1,2-dihydro-1,3-diphenyl-4-methyl-2-thioxo-pyrimidinium, 1,2-dihydro-3,4-dimethyl-2-oxo-quinazolinium and 1,2-dihydro-3,4-dimethyl-2-thioxo-quinazolinium. The compounds of the aforementioned group can be used to achieve particularly brilliant hair colorations.

As contemplated herein, it has been shown to be preferred if the CH-acid compound of the agent (B2) is selected from 1H-benzimidazol-2-ylacetonitrile (also known as 2-(cyanomethyl)-benzimidazole) and the physiologically tolerated salts of 1-allyl-1,2-dihydro-3,4,6-trimethyl-2-oxo-pyrimidinium and of 1,2-dihydro-1,3,4,6-tetramethyl-2-oxo-pyrimidinium and of mixtures of these compounds. Particularly preferred as contemplated herein are agents (B2) which necessarily comprise a salt of 1-allyl-1,2-dihydro-3,4,6-trimethyl-2-oxo-pyrimidinium and optionally 2-(cyanomethyl)benzimidazole.

The CH-acidic compounds of formula (CH-1) and/or of formula (CH-2) in the agent (B2) are preferably used in an amount of 0.03 to 65.00 mmol, based on 100 g of the agent (B2). The use of 1.00 to 30.00 mmol, based on 100 g of the agent (B2), is particularly preferred.

With regard to preferred combinations of reactive carbonyl compound and CH-acid compound of formula (CH-1) and/or formula (CH-2) in the agent (B2), explicit reference is made here to the disclosure document DE102008061863A1, paragraph [0156].

In the course of the work underlying the present disclosure, it was further shown that the various relevant shades can preferably be obtained from mixtures of the substances indicated in the following table in the indicated mixing ratio (indicated in % by weight):

| | Black | Brown | Copper | Red |
|---|---|---|---|---|
| 1-allyl-1,2-dihydro-3,4,6-trimethyl-2-oxopyrimidinium bromide | 10-15 | 0-12 | 0-10 | 0-10 |
| 1,2-dihydro-1,3,4,6-tetramethyl-2-oxopyrimidinium hydrogen sulfate | — | 0-5 | 0-10 | 0-10 |
| 2-(Cyanomethyl)-benzimidazole | 0-4 | 0-8 | 0-8 | 0-8 |
| 4-hydroxy-2-methoxybenzaldehyde | 0.5-4 | 0.5-5 | 0.5-15 | 0.5-15 |
| 3,4-dihydroxy-5-methoxybenzaldehyde | 8-15 | 0.5-10 | 0-0.5 | 0-0.5 |
| 2,3-Dihydro-1,5-dimethyl-3-oxo-2-phenyl-1H-pyrazol-4-carboxaldehyd | 0-6 | 0-6 | 0-8 | 0-6 |
| 2,4-Dimethoxy-benzaldehyde | 0-5 | 0-5 | 0-8 | 0-5 |
| 2-Chloro-3,4-dihydroxybenzaldehyde | 8-15 | 0.2-10 | 0-1.5 | 0-4 |
| 2-Bromo-3,4-dihydroxybenzaldehyde | 8-15 | 0.2-10 | 0-1.5 | 0-4 |

It was also found that the stability of the CH-acidic compounds used as contemplated herein can be increased if the agent (B2) has a pH in the range from about 0.5 to about 3, preferably in the range from about 1 to about 2.5, particularly preferably in the range from about 1.1 to about 1.9, in each case measured at 22° C. This measure increases the stability of the formulation to such an extent that there is no significant degradation of the CH-acid compound content even during storage for several months.

The pH in agents (B1) and (B2) can be adjusted using an organic or inorganic acid, such as hydrochloric acid, sulfuric acid, hydrobromic acid, phosphoric acid, acetic acid, tartaric acid, citric acid, lactic acid, malic acid or glycolic acid. In this context, the adjustment of the pH values as contemplated herein using sulfuric acid, hydrochloric acid, tartaric acid, citric acid, malic acid or lactic acid is particularly preferred.

In the method as contemplated herein, the agents (B1) and (B2) are intimately mixed together shortly before application to the hair fiber.

To further improve the coloring result, it is as contemplated herein to perform the CH-acid coloring of the second method step itself in a pH range of from about 7 to about 10, preferably in a pH range of from about 8 to about 9.5, particularly preferably at pH from about 8.5 to about 9, in each case measured at 22° C.

Therefore, a third agent (B3) comprising at least one alkalizing agent in a cosmetic carrier is added to the mixture of agents (B1) and (B2). As contemplated herein, it is preferred that the agent (B3) has a pH of from about 9 to about 14, particularly preferably from about 10 to about 12, in each case measured at 22° C.

The alkalizing agent included in agent (B3) in a cosmetic carrier is preferably selected from ammonia, basic amino acids, alkali hydroxides, alkanolamines, alkali metal metasilicates, urea, morpholine, N-methylglucamine, imidazole, alkali phosphates and alkali hydrogen phosphates. Preferred alkali metal ions are lithium, sodium, potassium, especially sodium or potassium.

The basic amino acids which can be used as alkalizing agents as contemplated herein are preferably selected from the group formed by L-arginine, D-arginine, D,L-arginine, L-histidine, D-histidine, D,L-histidine, L-lysine, D-lysine, D,L-lysine and the salts of these amino acids, in particular lysine hydrochloride. L-arginine is a particularly preferred alkalizing agent as contemplated herein.

The alkali hydroxides that can be used as alkalizing agents as contemplated herein are preferably selected from sodium hydroxide and potassium hydroxide and mixtures thereof. The alkanolamines that can be used as alkalizing agents as contemplated herein are preferably selected from primary amines having a $C_2$-$C_6$ alkyl parent carrying at least one hydroxyl group. Particularly preferred alkanolamines are selected from 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, 2-amino-2-methylpropan-1-ol (AMP), triethanolamine, triisopropanolamines (1,1',1"-nitrilotris-2-propanol), tromethamines (2-amino-2-(hydroxymethyl)-1,3-propanediol), tetrahydroxypropyl ethylenediamines, and mixtures of these compounds. Alkanolamines very particularly preferred as contemplated herein are selected from the group of 2-aminoethan-1-ol, 2-amino-2-methylpropan-1-ol (AMP), triethanolamine, 2-amino-2-methylpropan-ol and 2-amino-2-methylpropane-1,3-diol, as well as mixtures of these compounds.

Particularly preferably, the alkalizing agent is selected from at least one compound selected from the group of 2-aminoethan-1-ol (monoethanolamine), 2-amino-2-methylpropan-1-ol, 2-amino-2-methylpropane-1,3-diol, potassium hydroxide, sodium hydroxide, and L-arginine and mixtures thereof.

Furthermore, buffer systems adjusted to a pH value greater than about 7 can also be used in agent (B3).

As contemplated herein, a pH buffer system is a chemical compound or combination of chemical compounds which, in a solution, causes the pH of the solution to change only slightly when a small amount of acid or alkali is added to a volume of the cosmetic carrier. This change is less pronounced than is the case when the same amount of acid or alkali is added to an equal volume of cosmetic carrier without a pH buffer system.

Such pH buffer systems are preferably selected from at least one member of the group formed by hydrogen carbonate/carbonate, edible acid (in particular citric acid)/monohydrogen phosphate, edible acid (in particular citric acid)/dihydrogen phosphate, Tris(hydroxymethyl)aminomethane/maleic acid/NaOH, tris(hydroxymethyl)aminomethane/maleic acid/KOH, tris hydroxymethyl)aminomethane/HCl, monohydrogen phosphate/dihydrogen phosphate, dihydrogen phosphate/NaOH, dihydrogen phosphate/KOH, buffer system according to Theorell and Stenhagen, buffer system according to McIlvine, glycine/NaOH and glycine/KOH. Particularly preferred pH buffer systems are selected from at least one member of the group formed from tris(hydroxymethyl)aminomethane/maleic acid/NaOH, tri s (hydroxymethyl)aminomethane/maleic acid/KOH, and tris(hydroxymethyl)aminomethane/HCl.

The pH buffer systems marked with the slash from the above list represent mixtures of these compounds separated by the slash. The anionic compounds given in the list are used in the form of their salts with a corresponding monovalent or polyvalent cation. Preferred cations are alkali metal cations (especially sodium or potassium) and ammonium ions.

Edible acids that can be used in the buffer systems as contemplated herein are, for example, citric acid, tartaric acid or malic acid or mixtures thereof.

The pH buffer system is preferably present in the ready-to-use colorant in an amount of from about 0.1 to about 10.0% by weight, particularly preferably from about 0.3 to about 5.0% by weight, most preferably from about 0.5 to about 3.0% by weight, in each case based on the weight of the application mixture of agent (B1), agent (B2) and agent (B3).

In this context, the pH of the final application mixture prepared by mixing agents (B1), (B2) and (B3) with each other is in the range of from about 7 to about 10, preferably in the range of from about 8 to about 9.5, particularly preferably in the range of from about 8.5 to about 9, each measured at 22° C.

The compositions used in the method as contemplated herein comprise the components essential to the present disclosure in a cosmetically acceptable carrier. As such, a suitable aqueous, alcoholic or aqueous-alcoholic carrier is preferably used. For the purpose of the present disclosure, such carriers are, for example, creams, emulsions, gels or even surfactant-comprising foaming solutions, such as shampoos, foam aerosols or other preparations suitable for application to the hair. However, it is also conceivable to integrate the components essential to the present disclosure into a powder or tablet formulation.

For the purposes of the present disclosure, aqueous alcoholic solutions are understood to be aqueous solutions comprising from about 3 to about 70% by weight of a $C_1$-$C_4$ alcohol, in particular ethanol or isopropanol. The compositions as contemplated herein may additionally comprise further organic solvents, such as methoxybutanol, benzyl alcohol, ethyl diglycol or 1,2-propylene glycol. Preferred solvents are all water-soluble organic solvents.

In a first preferred embodiment, the agents (B1), (B2) and (B3) used as contemplated herein are adjusted to low viscosity. Application preparations which, after mixing components (B1), (B2) and (B3), have a viscosity of from about 10 to about 2000 mPas (measured at 22° C. in a Brookfield viscometer with spindle 4 and a speed of 4 rpm) have been found to be particularly preferred. A viscosity of 10 to 1000 mPas, measured under the above conditions, is particularly preferred as contemplated herein. A viscosity of from about 50 to about 500 mPas (measured at 20° C. (Brookfield viscometer type RV-T, spindle 4 with a rotational speed of 20 rpm)) is particularly preferred as contemplated herein.

Furthermore, it is essential to the present disclosure that the actual agent (B) is prepared only immediately before use by mixing the preparations (B1), (B2) and (B3). In order to carry out a mixture of preparations (B1), (B2) and (B3), there are a variety of possibilities, which have already been described in detail in WO 2010/046256 A2, to which explicit reference is made herein, and the contents incorporated by reference herein.

In a second preferred embodiment of the present disclosure, the agents (B1), (B2) and (B3) used in the method are of medium viscosity. Application preparations which, after mixing components (B1), (B2) and (B3), have a viscosity of from about 150 to about 15,000 mPas (measured at 22° C. in a Brookfield viscometer with spindle 4 and a speed of 4 rpm) have been found to be particularly preferred. A viscosity of from about 500 to about 5000 mPas, measured under the above conditions, is particularly preferred as contemplated herein.

In a third preferred embodiment of the present disclosure, the agents (B1), (B2) and (B3) used in the method are adjusted to be highly viscous. Application preparations which, after mixing components (B1), (B2) and (B3), have a viscosity of from about 500 to about 20,000 mPas (measured at 22° C. in a Brookfield viscometer with spindle 4 and a speed of 4 rpm) have been found to be particularly preferred. A viscosity of from about 1,000 to about 5,000 mPas, measured under the above conditions, is particularly preferred as contemplated herein In the context of this embodiment, it has proven advantageous to package the agents (B1), (B2) and (B3) in tubes.

Method Step 3: Oxidative Color Proof

After dye removal, the keratin-comprising fiber should be as completely freed as possible from its applied CH-acid dyeing, receive no or as little damage as possible to the fiber structure and, in particular, have softness and good combability.

Surprisingly, it has now been found that hydrogen peroxide-comprising decolorizers provide excellent color removal of keratin-comprising fibers dyed with CH-acid dyeing, while protecting the fibers. The use of organic peroxo compounds and inorganic persalts can be dispensed with. In addition, the fiber-preserving decolorization of the CH-acid dyeing succeeds already with the use of small amounts of hydrogen peroxide or after a reaction time of from about 3 to about 45 minutes, preferably from about 5 to about 30 minutes, particularly preferably from about 10 to about 20 minutes.

The decolorizing agent (Ox) of the method as contemplated herein comprises hydrogen peroxide in a cosmetic carrier.

Decolorizing agents (Ox) preferably used as contemplated herein comprise hydrogen peroxide in an amount of from about 0.5 to about 12% by weight, preferably in an amount of 1 to about 6% by weight, particularly preferably in an amount of from about 1 to about 4% by weight, most preferably in an amount of from about 1.5 to about 3% by weight, each calculated on the weight of the total decolorizing agent (Ox).

The decolorizing agent (Ox) preferably has a pH of from about 4 to about 11, more preferably from about 5 to about 10, most preferably from about 7 to about 10.

Furthermore, it is preferred as contemplated herein if the decolorizing agent (Ox) comprises less than about 0.001% by weight of further peroxo compounds in addition to hydrogen peroxide, i.e. is free from further peroxo compounds as contemplated herein. Peroxo compounds are chemical compounds comprising the group —O— or O22- in the molecule.

The further peroxo compounds defined in the context of this embodiment of the decolorizing agent (Ox) do not include hydrogen peroxide and thus do not include perhydrates. Preferred peroxo compounds to be avoided are organic peracids, peroxodisulfate salts, persulfate salts, peroxodiphosphate salts (especially ammonium peroxodisulfate, potassium peroxodisulfate, sodium peroxodisulfate, ammonium persulfate, potassium persulfate, sodium persulfate, potassium peroxodiphosphate) and peroxides (such as barium peroxide and magnesium peroxide). Therefore, those decolorizing agents (Ox) which are free from organic peracids and peroxodisulfate salts and persulfate salts and peroxodiphosphate salts and peroxides are particularly preferred.

As contemplated herein, it is preferred if the decolorizing agent (Ox) additionally comprises at least one surfactant. In many cases, the ready-to-use decolorants comprise at least one surfactant, and in principle both anionic and zwitterionic, ampholytic, nonionic and cationic surfactants are suitable. In many cases, however, it has proven advantageous to select surfactants from anionic, zwitterionic or nonionic surfactants.

As contemplated herein, it is preferred to leave the decolorizing agent on the fiber for about 3 to about 45 minutes, preferably from about 5 to about 30 minutes, particularly preferably from about 10 to about 20 minutes.

Furthermore, it was demonstrated in the course of the work on the present application that the observed effects can be further enhanced if the compositions as contemplated herein additionally comprise at least one optionally ethoxylated and/or propoxylated fatty alcohol.

By optionally ethoxylated and/or propoxylated fatty alcohols are meant, as contemplated herein, addition products of from about 0 to about 30 moles of ethylene oxide, preferably from about 2 to about 25 moles of ethylene oxide, in particular of from about 10 to about 20 moles of ethylene oxide and/or from about 0 to about 5 moles of propylene oxide to linear fatty alcohols comprising 8 to 22 carbon atoms.

Typical examples of fatty alcohols preferred as contemplated herein are caprylic alcohol, capryl alcohol, 2-ethylhexyl alcohol, caprin alcohol, lauryl alcohol, isotridecyl alcohol, myristyl alcohol, cetyl alcohol, palmoleyl alcohol, stearyl alcohol, Isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol, and technical mixtures thereof, which are used, for example, in high-pressure hydrogenation. E.g. from the high-pressure hydrogenation of technical methyl esters based on fats and oils or aldehydes from Roelen's oxosynthesis and as monomer fraction from the dimerization of unsaturated fatty alcohols. Particularly preferred are technical fatty alcohols with 12 to 18 carbon atoms, such as coconut, palm, palm kernel or tallow fatty alcohols.

The addition of fatty alcohol ethoxylates, such as ceteareth-12, ceteareth-20 and ceteareth-30, has proven to be quite preferred.

Furthermore, as contemplated herein, it has proved particularly advantageous for achieving the optimum effects, in particular uniform and intensive color buildup, if the agents used in the methods as contemplated herein comprise a solubilizer.

Particularly advantageous solubilizers as contemplated herein are
a) Glycerol mono- and diesters and sorbitan mono- and diesters of saturated and unsaturated fatty acids comprising 6 to 22 carbon atoms and their ethylene oxide addition products;

b) Addition products of 15 to 60 mol ethylene oxide to castor oil and/or cured castor oil, and c) Addition products of 20 to 30 moles of ethylene oxide and/or 20 to 20 moles of propylene oxide to linear fatty alcohols comprising 4 to 8 carbon atoms and to alkylphenols comprising 8 to 15 carbon atoms in the alkyl group.

Preferred solubilizers of group a) are, for example, ethoxylated sorbitan monoesters of lauric acid or oleic acid, as known, for example, under the INCI designations polysorbate-20 and polysorbate-80.

Preferred solubilizers of group b) are, for example, addition products of about 40 mol ethylene oxide to hydrogenated castor oil, such as those commercially available under the INCI designation PEG-40 Hydrogenated Castor Oil.

As contemplated herein, it has proved advantageous if the agents used comprise at least two solubilizers from different groups a) to c).

Moreover, it has been shown to be particularly preferred if the solubilizers are included in the agent (B1) comprising at least one reactive carbonyl compound.

The solubilizers are preferably present in the compositions used as contemplated herein in an amount of from about 0.1 to about 10% by weight, in particular from about 0.5 to about 6% by weight, based on the respective composition.

Furthermore, the agents used in the method as contemplated herein may comprise all active ingredients, additives and auxiliaries known in such preparations. In many cases, the ready-to-use colorants comprise at least one surfactant, with anionic as well as zwitterionic, ampholytic, nonionic and cationic surfactants being suitable in principle. In many cases, however, it has proven advantageous to select surfactants from anionic, zwitterionic or nonionic surfactants.

Preferred anionic surfactants are alkyl sulfates, alkyl polyglycol ether sulfates and ether carboxylic acids with 10 to 18 carbon atoms in the alkyl group and up to 12 glycol ether groups in the molecule and, in particular, salts of saturated and especially unsaturated $C_8$-$C_{22}$ carboxylic acids, such as oleic acid, stearic acid, isostearic acid and palmitic acid.

The term zwitterionic surfactants is used to describe surface-active compounds that carry at least one quaternary ammonium group and at least one $—COO^{(-)}$ or $—SO_3(^-)$ group in the molecule. Particularly suitable zwitterionic surfactants are the so-called betaines such as the N-alkyl-N,N-dimethylammonium glycinates, for example cocoalkyl dimethylammonium glycinate, N-acylaminopropyl-N,N-dimethylammonium glycinates, for example cocoacylaminopropyl dimethylammonium glycinate, and 2-alkyl-3-carboxymethyl-3-hydroxyethyl imidazolines each having 8 to 18 carbon atoms in the alkyl or acyl group, and the cocoacylaminoethyl hydroxyethyl carboxymethyl glycinate. A preferred zwitterionic surfactant is the fatty acid amide derivative known by the CTFA name cocamidopropyl betaine. Ampholytic surfactants are surface-active compounds which, in addition to a $C_{8-18}$ alkyl or acyl group in the molecule, comprise at least one free amino group and at least one $—COOH$ or $—SO_3H$ group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having about 8 to 18 carbon atoms in the alkyl group. Particularly preferred ampholytic surfactants are N-cocosalkylaminopropionate, cocosacylaminoethylaminopropionate and $C_{12-18}$ acyl sarcosine.

Non-ionic surfactants comprise, for example, a polyol group, a polyalkylene glycol ether group or a combination of polyol and polyglycol ether group as the hydrophilic group. Such connections are for example Addition products of 2 to 30 moles of ethylene oxide and/or 0 to 5 moles of propylene oxide to linear fatty alcohols comprising 8 to 22 carbon atoms, to fatty acids comprising 12 to 22 carbon atoms and to alkylphenols comprising 8 to 15 carbon atoms in the alkyl group, $C_{12}$-22 fatty acid mono- and diesters of addition products of 1 to 30 moles ethylene oxide to glycerol, $C_8$-22 alkyl mono- and oligoglycosides and their ethoxylated analogues, Addition products of ethylene oxide to fatty acid alkanolamides.

Examples of the cationic surfactants that can be used in the method as contemplated herein are, in particular, quaternary ammonium compounds. Preferred ammonium halides include alkyltrimethylammonium chlorides, dialkyldimethylammonium chlorides and trialkylmethylammonium chlorides, e.g., cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. Other cationic surfactants that can be used as contemplated herein are the quaternized protein hydrolysates.

Also suitable as contemplated herein are cationic silicone oils such as the commercially available products Q2-7224 (manufacturer: Dow Corning; a stabilized trimethylsilylamodimethicone), Dow Corning 929 Emulsion (comprising a hydroxyl-amino-modified silicone also known as amodimethicone), SM-2059 (Manufacturer: General Electric), SLM-55067 (Manufacturer: Wacker) and Abil®-Quat 3270 and 3272 (manufacturer: Th. Goldschmidt; diquaternary polydimethylsiloxanes, quaternium-80).

Examples of surfactants that can be used in the method as contemplated herein continue to be alkylamidoamines, in particular fatty acid amidoamines such as the stearylamidopropyldimethylamine available under the name Tego Amid® S 18, which, in addition to a good conditioning effect, are exemplified in particular by their good biodegradability.

Examples of cationic surfactants that can be used in the method as contemplated herein are furthermore quaternary ester compounds, so-called "esterquats", such as the methylhydroxyalkyldialkoyloxyalkylammonium methosulfates marketed under the trademark Stepantex®, which are very readily biodegradable.

The compounds with alkyl groups used as surfactants may be uniform substances in each case. However, it is usually preferable to start from native vegetable or animal raw materials for the production of these substances, so that substance mixtures with different alkyl chain lengths dependent on the respective raw material are obtained.

The ingredients of the cosmetic carrier are used in agents A, (B1), (B2), (B3) and (Ox) in amounts customary for this purpose; for example, emulsifiers are present in concentrations of from about 0.5 to about 30% by weight and thickeners in concentrations of from about 0.1 to about 25% by weight, based on the respective agent.

The following examples are intended to explain the subject matter of the present disclosure in more detail, but without limiting it in any way.

Unless otherwise stated, the quantities used in the examples are in percent by weight.

Method Step 1: Oxidative Colorant (A)

The following coloring cream (A1) was prepared:

| Ingredient | Amount (% by weight) |
|---|---|
| Cetearyl alcohol | 13.2 |
| Ceteareth-20 | 3.4 |
| Ammonium hydroxide | 2.4 |
| Monoethanolamine | 0.6 |
| Potassium hydroxide | 0.1 |
| Glyceryl stearate | 2.0 |
| 2-octyldodecanol | 2.2 |
| Sodium laureth sulfate | 1.3 |
| Glycerin | 0.8 |
| Sodium cetearyl sulfate | 0.7 |
| Oleic acid | 0.4 |
| Sodium sulfite | 0.4 |
| Perfume | 0.4 |
| Silica | 0.25 |
| Tetrasodium EDTA | 0.2 |
| Carbomer | 0.2 |
| Potassium stearate | 0.2 |
| 1-Hydroxyethyl-4,5-diaminopyrazole sulfate | 1.5 |
| 4-Amino-3-methylphenol | 0.18 |
| 4-Amino-2-methylphenol | 0.30 |
| m-Aminophenol | 0.6 |
| Polyquaternium-39 | 0.1 |
| Ascorbic acid | 0.1 |
| Sodium sulfate | 0.1 |
| Linoleamidopropyl PG-Dimonium Chloride Phosphate | 0.03 |
| Benzyl salicylate | 0.02 |
| Moringa Pterygosperma Seed Extract | 0.005 |
| Citric acid | 0.002 |
| Titanium dioxide | 0.5 |
| Water | ad 100 |

The following oxidant preparation (A2) was prepared:

| Ingredient | Amount (% by weight) |
|---|---|
| Sodium benzoate | 0.04 |
| Dipicolinic acid | 0.10 |
| Disodium pyrophosphate | 0.10 |
| Potassium hydroxide (50% by weight) | 0.20 |
| Propanediol-1,2 | 0.50 |
| Turpinal ® SL | 0.25 |
| Paraffinum Liquidum | 2.00 |
| Cetearyl alcohol | 3.60 |
| Ceteareth-20 | 1.20 |
| Hydrogen peroxide (50% by weight) | 12.20 |
| Water, demineralized | ad 100.00 |

Oxidative Hair Coloring

Immediately before application to the hair, 60 g of coloring cream (A1) was mixed with 60 g of the oxidant preparation (A2) and applied to the hair to be colored. After an exposure time of 30 minutes at 32° C., the mixture was thoroughly rinsed from the hair strands with lukewarm water, the strands were cleaned again with a commercial shampoo and then dried in a warm air stream (30 to 40° C.).

The dyed hair had an intense dark blond-red color.

One week later, this oxidatively dyed hair was dyed with a CH-acid dye (B) as described below.

Method Step 2: CH-Acid Dye (B)

Agent (B1) comprising reactive carbonyl compounds

| Ingredient | Amount (% by weight) |
|---|---|
| Cetearyl alcohol | 9.45 |
| Lorol techn. | 3.15 |
| Ceteareth-20 | 2.52 |
| 3,4-dihydroxy-5-methoxybenzaldehyde | 1.17 |
| 4-formyl-1-methylquinolinium-p-toluenesulfonate | 1.14 |
| 2,3-dihydro-1,5-dimethyl-3-oxo-2-phenyl-1H-pyrazole-4-carboxaldehyde (antipyrinecarboxaldehyde) | 0.54 |
| Ascorbic acid | 0.63 |
| Sodium sulfite | 0.13 |
| Turpinal ® SL | 0.25 |
| Sodium silicate 40/42 (sodium silicate) | 0.63 |
| Perfume | 0.38 |
| Phenoxyethanol | 1.00 |
| Sodium salicylate | 0.50 |
| Water, demineralized | ad 100.00 |
| pH 3-4 (22° C.) | |

Agent (B2) in gel form, comprising CH-acid compounds of the formulae (CH-1) and (CH-2)

| Ingredient | Amount (% by weight) |
|---|---|
| 1-Allyl-1,2-dihydro-3,4,6-trimethyl-2-oxopyrimidinium bromide [Formula (CH-1)] | 2.94 |
| 1H-benzimidazol-2-ylacetonitrile (2-(cyanomethyl)benzimidazole) [Formula (CH-2)] | 0.19 |
| Hydroxyethylcellulose | 1.58 |
| Tartaric acid/monoethanolamine | @ pH 1-3 |
| Water, demineralized | ad 100.00 |

Agent (B3) comprising alkalizing agent

| Ingredient | Amount (% by weight) |
|---|---|
| Monoethanolamine | 20.00 |
| Water, demineralized | 80.00 |

The mixing ratio (B1):(B2):(B3) by mass was 10:10:1.

Components (B1) and (B2) were homogeneously mixed together, then the alkalizing component (B3) was added and homogeneously mixed in, taking into account the mass mixing ratio (B1):(B2):(B3) given above as 10:10:1.

The mixture obtained had a pH of 9, measured at 22° C.

As soon as the alkalizing agent (B3) was added to the mixture of (B1) and (B2), the reaction between the reactive carbonyl compounds and the CH-acidic substances started.

The finished mixture of the three components was applied directly after the mixing process to the hair that had been oxidatively dyed a week earlier, as described above.

After an exposure time of 30 minutes at 32° C., the CH-acid dye was thoroughly rinsed from the hair strands, which were cleaned again with a commercial shampoo and then dried in a warm air stream (30 to 40° C.).

The hair was now an intense mahogany-brown color.

Method Step 3: Oxidative Decolorization (Ox) of the CH-Acid Coloring

The oxidative decolorizing agent (Ox) for decolorizing the CH-acid dye is prepared just before application to the hair by mixing an acidic gel comprising hydrogen peroxide (Ox-1) with the alkalizing agent (B3) as described above for alkalizing the CH-acid dye in a mass mixing ratio of 1:1.

The acidic gel comprising hydrogen peroxide (Ox-1) is composed as follows:

| Ingredient | Amount (% by weight) |
| --- | --- |
| Sodium hydroxide (50% by weight) | 1.20 |
| Dipicolinic acid | 0.18 |
| Disodium pyrophosphate | 0.05 |
| Turpinal ® SL | 2.70 |
| Keltrol CG-SFT | 3.60 |
| Propanediol-1,2 | 7.20 |
| Hydrogen peroxide (50% by weight) | 21.80 |
| Water, demineralized | ad 100.00 |

The oxidative decolorizing agent (Ox) used to decolorize the CH-acid coloring has a pH of 10 (22° C.) and is composed as follows:

| Ingredient | Amount (% by weight) |
| --- | --- |
| Sodium hydroxide (50% by weight) | 0.60 |
| Dipicolinic acid | 0.09 |
| Disodium pyrophosphate | 0.025 |
| Turpinal ® SL | 1.35 |
| Keltrol CG-SFT | 1.80 |
| Propanediol-1,2 | 3.60 |
| Hydrogen peroxide (50% by weight) | 10.90 |
| Monoethanolamine | 10.00 |
| Water, demineralized | ad 100.00 |

Decolorization

Two days after dyeing with a CH-acid dye (B), as described below, this hair was oxidatively decolorized again.

For decolorization, the hair was soaked with the preceding decolorizing agent (Ox). The liquor ratio was 3:1 (grams of decolorant per gram of hair).

After an exposure time of 10 minutes at 32° C., the decolorizing agent was thoroughly rinsed from the hair strands, which were cleaned again with a commercial shampoo and then dried in a warm air stream (30 to 40° C.).

Colorimetric Measurements

The color result of each of the three aforementioned method steps of the process as contemplated herein was determined in each case one day after the dyeing or decolorizing process by measuring the CIE Lab values with the Texaflash DC 3881 device from Datacolor.

The color differences ΔE between the dyed and the decolorized hair strand result from the respective CIE Lab values according to the color difference formula given below.

$$\Delta E = \left[ (\Delta L)^2 + (\Delta a)^2 + (\Delta b)^2 \right]^{\frac{1}{2}} \text{ (color distance formula)}$$

The table below summarizes the measured CIE Lab values and the calculated color distance of the coloring removal tests according to the method of the present disclosure.

| | CIE L Std. | CIE a Std. | CIE b Std. | ΔE |
| --- | --- | --- | --- | --- |
| Color result of oxidative coloring | 26.61 | 31.52 | 15.98 | |
| Color result after oxidative coloring and CH-acid coloring | 18.40 | 9.09 | 3.90 | 26.77 |
| Color result after oxidative stripping of the CH-acid coloring | 29.73 | 28.61 | 18.34 | 4.88 |

After oxidative stripping of the CH-acid dyeing, i.e., the end of the third method step of the process as contemplated herein, the color difference between the original color result of the oxidative dyeing and the color result of the oxidative dyeing after intermediate on/off coloration with the CH-acid dyeing agent was 4.88. This ΔE value shows a sufficiently small color distance to the original color result.

The method as contemplated herein is thus excellently suited for intermediate overcoloring of a permanent oxidative hair coloration and for returning to the original color result after a gentle oxidation process.

List of Trading Products Used

The trading products used in the examples are defined as follows:
Akypo Soft 45 NV® lauryl alcohol-4.5-EO acetic acid sodium salt (21% active ingredient content by weight; INCI designation: Sodium Laureth-6 Carboxylate) (Kao Corporation)
Cremophor® RH40 hydrogenated castor oil with 40 EO units (INCI designation: PEG-40 Hydrogenated Castor Oil) (BASF)
Crodafos® CES INCI designation: Cetearyl Alcohol, Dicetyl Phosphate, Ceteth-10 Phosphate (Croda)
Eumulgin® B1 cetylstearyl alcohol with 12 EO units (INCI: Ceteareth-12) (BASF)
Hydrenol® D $C_{16-18}$ fatty alcohol (INCI designation: Cetearyl alcohol) (BASF)
Keltrol CG-SFT Xanthan Gum (CP Kelco)
Lorol® tech. $C_{12-18}$ fatty alcohol (INCI designation: Coconut alcohol) (BASF)
Plantacare® 2000 $C_{8-16}$ alkyl glucoside (53 wt % active ingredient content in water; INCI designation: Decyl Glucoside, Aqua (Water)) (BASF)
Synthalen® K polyacrylic acid (approx. 89% active ingredient content; INCI designation: Carbomer) (3V Sigma)
Texapon® NSO lauryl ether sulfate, sodium salt (approx. 27.5% active ingredient; INCI designation: Sodium Laureth Sulfate) (BASF)
Turpinal® SL 1-hydroxyethane-1,1-diphosphonic acid (approx. 58-61 wt. % active ingredient content; INCI designation: Etidronic Acid, Aqua (Water)) (Solutia)
Carbopol® Ultrez 10 polyacrylate (INCI designation: Carbomer) (Lubrizol)

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodi-

The invention claimed is:
1. A method for dyeing hair, comprising:
(1) treating hair with an oxidative colorant agent (A);
(2) subsequent to (1), treating the hair with a CH-acidic hair dyeing agent (B),
wherein the CH-acidic hair dyeing agent (B) has a pH of from about 7 to about 10, measured at 22° C., and comprises the product of mixing together three agents (B1), (B2), and (B3), where
agent (B1) comprises at least one reactive carbonyl compound in a cosmetic carrier and is free from CH-acidic compounds,
agent (B2) comprises at least one CH-acidic compound in a cosmetic carrier and is free from reactive carbonyl compounds, the at least one CH-acidic compound being selected from compounds of the formula (CH-1) and/or compounds of the formula (CH-2):

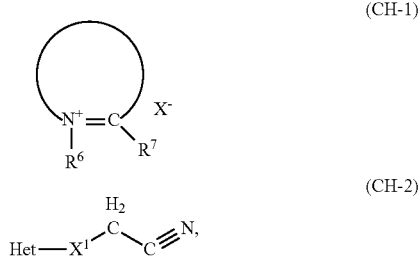

wherein in formula (CH-1):
$R^6$ represents a linear or cyclic ($C_1$ to $C_6$)alkyl group; a ($C_2$ to $C_6$)alkenyl group; an optionally substituted aryl group; an optionally substituted heteroaryl group; an aryl ($C_1$ to $C_6$)alkyl group; a ($C_1$ to $C_6$)hydroxyalkyl group; a ($C_2$ to $C_6$)polyhydroxyalkyl group; a ($C_1$ to $C_6$)alkoxy ($C_1$ to $C_6$)alkyl group; a group of the formula $R^I R^{II} N\!-\!(CH_2)_m\!-\!$, in which m is an integer of from 2 to 6, and $R^I$ and $R^{II}$ each independently of one another represent a hydrogen atom, a ($C_1$ to $C_4$)alkyl group, a ($C_1$ to $C_4$)hydroxyalkyl group, or an aryl-($C_1$ to $C_6$)alkyl group, it being where $R^I$ and $R^{II}$ together with the nitrogen atom N optionally form a 5-, 6-, or 7-membered ring,
$R^7$ represents a ($C_1$ to $C_6$)alkyl group, and
$X^-$ is a physiologically compatible anion, and
where the formula (CH-1) represents a heterocyclic structure optionally comprising nitrogen, oxygen, and/-or sulfur heteroatoms in a ring structure between N-$R^6$ and C-$R^7$-, where the ring structure may be fused to another ring structure, and where each ring structure in the compound of the formula (CH-1) is optionally substituted with a pendant substituent; and
wherein in (CH-2):
Het represents an optionally substituted heteroaromatic group, and
$X^1$ represents a covalent bond or a carbonyl group (C=O); and
agent (B3) comprises at least one alkalizing agent; and (3) subsequent to (2), treating the hair with a cosmetic decolorizing agent (Ox),
wherein the cosmetic decolorizing agent (Ox) has a pH value in the range from 4 to 11, measured at 22° C., and comprises water and from about 0.5 to about 12 wt. % hydrogen peroxide, based on the total weight of the decolorizing agent (Ox);
wherein the method comprises a time interval between (1) and (2) of from about 1 minute to about 1.5 months, and a time interval between (2) and (3) of from about 1 minute to about 1.5 months.

2. The method of claim 1, wherein (1) further comprises preparing the oxidative colorant agent (A) immediately before use from an agent (A1) comprising at least one oxidation dye precursor and an agent (A2) comprising at least one oxidizing agent.

3. The method of claim 1, wherein the agent (B1) comprises a reactive carbonyl compound selected from 4-hydroxy-3-methoxybenzaldehyde, 3,5-dimethoxy-4-hydroxybenzaldehyde, 4-hydroxy-1-naphthaldehyde, 4-hydroxy-2-methoxybenzaldehyde, 3,4-dihydroxy-5-methoxybenzaldehyde, 3,4,5-trihydroxybenzaldehyde, 3,5-dibromo-4-hydroxybenzaldehyde, 4-hydroxy-3-nitrobenzaldehyde, 3-bromo-4-hydroxybenzaldehyde, 4-hydroxy-3-methylbenzaldehyde, 3,5-dimethyl-4-hydroxybenzaldehyde, 5-bromo-4-hydroxy-3-methoxybenzaldehyde, 4-di ethyl amino-2-hydroxybenzaldehyde, 4-dimethyl amino-2-methoxybenzaldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxy-benzaldehyde, 4-hydroxy-2,5-dimethoxy-benzaldehyde, 4-hydroxy-2,6-dimethoxy-benzaldehyde, 4-hydroxy-2-methyl-benzaldehyde, 4-hydroxy-2,3-dimethyl-benzaldehyde, 4-hydroxy-2,5-dimethyl-benzaldehyde, 4-hydroxy-2,6-dimethyl-benzaldehyde, 3,5-diethoxy-4-hydroxy-benzaldehyde, 2,6-diethoxy-4-hydroxy-benzaldehyde, 3-hydroxy-4-methoxy-benzaldehyde, 2-hydroxy-4-methoxy-benzaldehyde, 2-ethoxy-4-hydroxy-benzaldehyde, 3-ethoxy-4-hydroxy-benzaldehyde, 4-ethoxy-2-hydroxybenzaldehyde, 4-ethoxy-3-hydroxy-benzaldehyde, 2,3-dimethoxybenzaldehyde, 2,4-dimethoxybenzaldehyde, 2,5-dimethoxybenzaldehyde, 2, 6-dimethoxybenzaldehyde, 3,4-dimethoxybenzaldehyde, 3,5-dimethoxybenzaldehyde, 2,3, 4-trimethoxybenzaldehyde, 2,3,5-trimethoxybenzaldehyde, 2,3, 6-trimethoxybenzaldehyde, 2,4, 6-trimethoxybenzaldehyde, 2,4,5-trimethoxybenzaldehyde, 2,5, 6-trimethoxybenzaldehyde, 2-hydroxybenzaldehyde, 3-hydroxybenzaldehyde, 4-hydroxybenzaldehyde, 2,3-dihydroxybenzaldehyde, 2,4-dihydroxybenzaldehyde, 2,4-dihydroxy-3-methyl-benzaldehyde, 2,4-dihydroxy-5-methyl-benzaldehyde, 2,4-dihydroxy-6-methyl-benzaldehyde, 2,4-dihydroxy-3-methoxybenzaldehyde, 2,4-dihydroxy-5-methoxy-benzaldehyde, 2,4-dihydroxy-6-methoxy-benzaldehyde, 2,5-dihydroxybenzaldehyde, 2, 6-dihydroxybenzaldehyde, 3,4-dihydroxybenzaldehyde, 3,4-dihydroxy-2-methyl-benzaldehyde, 3,4-dihydroxy-5-methyl-benzaldehyde, 3,4-dihydroxy-6-methyl-benzaldehyde, 3,4-dihydroxy-2-methoxybenzaldehyde, 3,5-dihydroxybenzaldehyde, 2,3,4-tri hydroxybenzaldehyde, 2,3,5-trihydroxybenzaldehyde, 2,3, 6-tri hydroxybenzaldehyde, 2,4,6-tri hydroxybenzaldehyde, 2,4,5-trihydroxybenzaldehyde, 2,5,6-tri hydroxybenzaldehyde, 4-dimethyl aminobenzaldehyde, 4-diethylaminobenzaldehyde, 4-dimethyl amino-2-hydroxybenzaldehyde, 4-pyrrolidinobenzaldehyde, 4-morpholinobenzaldehyde, 2-morpholinobenzaldehyde, 4-piperidinobenzaldehyde, 3,5-dichloro-4-hydroxybenzaldehyde, 4-hydroxy-3,5-diiodobenzaldehyde, 3-chloro-4-hydroxybenzaldehyde, 5-chloro-3,4-dihydroxybenzaldehyde, 5-bromo-3,4-dihydroxybenzaldehyde, 3-chloro-4-hydroxy-5-methoxybenzaldehyde, 4-hydroxy-3-iodo-5-methoxybenzaldehyde, 2-methoxy-1-naphthaldehyde, 4-methoxy-1-naphthaldehyde, 2-hydroxy- 1-naphthaldehyde, 2,4-dihydroxy- 1-naphthaldehyde, 4-hydroxy-3-methoxy- 1-naphthaldehyde, 2-hydroxy-4-methoxy-1-naphthaldehyde, 3-hydroxy-4-methoxy- 1-naphthaldehyde, 2,4-dimethoxy- 1-naphthaldehyde, 3,4-dimethoxy-1-naphthaldehyde, 4-dimethyl amino- 1-naphthaldehyde, 3-hydroxy-4-nitrobenzaldehyde, 2-hydroxy-3-methoxy-5-nitrobenzaldehyde, 5-nitrovanillin, 2,5-dinitrosalicylaldehyde, 5-bromo-3-nitrosalicylaldehyde, 2-dimethylaminobenzaldehyde, 2-chloro-4-dimethylaminobenzaldehyde, 4-dimethylamino-2-methylbenzaldehyde, 4-diethylaminocinnamaldehyde, 4-dibutylamino-benzaldehyde, 3-carboxy-4-hydroxy-benzaldehyde, 5-carboxyvanillin, 3-carboxy-4-hydroxy-5-methylbenzaldehyde, 3-carb oxy-5-ethoxy-4-hydroxybenzaldehyde, 3-carb oxy-4-hydroxybenzaldehyde, 5-carboxyvanillin, 3-carb oxy-4-hydroxy-5-methylbenzaldehyde, 3-carboxy-5-ethoxy-4-hydroxybenzaldehyde, 3-Allyl-4-hydroxybenzaldehyde, 3-Allyl-4-hydroxy-5-methoxybenzaldehyde, 3-Allyl-4-hydroxy-5-m ethylbenzaldehyde, 3-Allyl-5-bromo-4-hydroxybenzaldehyde, 3,5-di allyl-4-hydroxybenzaldehyde, 3-Ally1-5-carb oxy-4-hydroxybenzaldehyde (3-Allyl-5-formyl-2-hydroxybenzoic acid), 3-allyl-4-hydroxy-5-formylbenzaldehyde, 5-allyl-4-hydroxyisophthalaldehyde, 2,3-dihydro- 1,5-dimethyl-3-oxo-2-phenyl- 1H-pyrazole-4-carboxaldehyde, 4-formyl-1-methyl quinolinium-p-toluenesulfonate, and combinations thereof.

4. The method of claim 1, wherein the agent (B1) comprises a reactive carbonyl compound selected from 4-hydroxy-2-methoxybenzaldehyde, 2-chloro-3,4-dihydroxybenzaldehyde, 2-bromo-3,4-dihydroxybenzaldehyde, 3,4-dihydroxy-5-methoxybenzaldehyde, 2,3-dihydro- 1,5-dimethyl-3-oxo-2-phenyl- 1H-pyrazol e-4-carboxaldehyde, 2,4-dimethoxybenzaldehyde, 4-formyl- 1-methyl quinolinium-p-toluenesulfonate, and combinations thereof.

5. The method of claim 1, wherein the agent (B1) comprises, as the at least one reactive carbonyl compound, 4-formyl-1-methylquinolinium-p-toluenesulfonate and at least one of 3,4-dihydroxy-5-methoxybenzaldehyde, 2-chloro-3,4-dihydroxybenzaldehyde, 2-bromo-3,4-dihydroxybenzaldehyde, 3,4-dihydroxy-5-methoxybenzaldehyde, 2,3-dihydro- 1,5-dimethyl-3-oxo-2-phenyl-1H-pyrazole-4-carboxaldehyde, and 2,4-dimethoxy-benzaldehyde.

6. The method of claim 1, wherein the agent (B2) comprises a CH-acid compound selected from 1H-benzimidazol-2-ylacetonitrile, physiologically tolerated salts of 1-allyl-1,2-dihydro-3,4,6-trimethyl-2-oxo-pyrimidinium, physiologically tolerated salts of 1,2-dihydro-1,3,4,6-tetramethyl-2-oxo-pyrimidinium, and combinations thereof.

7. The method of claim 1, wherein the agent (B2) comprises a salt of 1-allyl-1,2-dihydro-3,4,6-trimethyl-2-oxo-pyrimidinium, and optionally additionally 1H-benzimidazol-2-ylacetonitrile (2-(cyanomethyl)benzimidazole).

8. The method of claim 1, wherein the agent (B1) has a pH of from about 2 to about 5, measured at 22° C.

9. The method of claim 1, wherein the agent (B2) has a pH of from about 0.5 to about 3, measured at 22° C.

10. The method of claim 1, wherein the time interval between (1) and (2) is from about 30 minutes to about 1 month.

11. The method of claim 1, wherein the time interval between (2) and (3) is from about 30 minutes to about 14 days.

12. The method of claim 1, wherein the agent (B3) comprises an alkalizing agent selected from ammonia, basic amino acids, alkali hydroxides, alkanolamines, alkali metal metasilicates, urea, morpholine, N-methylglucamine, imidazole, Alkali phosphates, alkali hydrogen phosphates, and combinations thereof.

13. The method of claim 2, wherein the agent (A1) comprises at least one developer component selected from the group of p-phenylenediamine, p-toluylenediamine, 2-(beta-hydroxyethyl)-p-phenylenediamine, 2-methoxymethyl-p-phenylenediamine, 2-(alpha, beta-dihydroxyethyl)-p-phenylenediamine, N,N-bis-(beta-hydroxyethyl)-p-phenylenediamine, N-(4-amino-3-methylphenyl)-N[3-(1H-imidazol-1-yl)propyl] amine, N,N'-bis-(beta-hydroxyethyl)-N,N'-bis-(4-aminophenyl)-1,3-diamino-propan-2-ol, bis-(2-hydroxy-5-aminophenyl)-methane, 1,3-bis-(2,5-diaminophenoxy)-propan-2-ol, N,N'-bis-(4-aminophenyl)-1,4-diazacycloheptane, 1, 10-bis-(2,5-diaminophenyl)-1,4, 7,10-tetraoxadecane, p-aminophenol, 4-amino-3-methylphenol, 4-amino-2-aminomethylphenol, 4-amino-2-(alpha, beta-dihydroxyethyl)-phenol and 4-amino-2-(diethylaminomethyl)-phenol, 4,5-diamino-1-(beta-hydroxyethyl)-pyrazole, 2,4,5,6-tetraaminopyrimidine, 4-hydroxy-2,5,6-triaminopyrimidine, 2-hydroxy-4,5,6-triaminopyrimidine, physiologically tolerated salts thereof, and combinations thereof.

14. The method of claim 13, wherein the agent (A1) further comprises at least one coupler component selected from m-aminophenol, 5-amino-2-methylphenol, 3-amino-2-chloro-6-methylphenol, 2-hydroxy-4-aminophenoxy ethanol, 5-amino-4-chloro-2-methylphenol, 5-(2'-hydroxyethyl)amino-2-methylphenol, 2,4-dichloro-3-aminophenol, o-aminophenol, m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino) ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2'-hydroxyethyl)-aminobenzene, Resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyriadine, 3,5-diamino-2,6-dimethoxypyriadine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, physiologically tolerated salts thereof, and combinations thereof.

15. The method of claim 2, wherein the agent (A2) comprises hydrogen peroxide as an oxidizing agent.

16. A process for multitonal dyeing of hair, comprising:
(1) preparing an oxidative colorant agent (A) from at least a developer component, a coupler component, and an oxidizing agent;
(2) treating hair with the oxidative colorant agent (A) prepared in (1) to give a colored hair;

(3) preparing a CH-acidic hair dyeing agent (B) having a pH of from about 7 to about 10, measured at 22° C., by mixing together:
   (B1) an agent comprising at least one reactive carbonyl compound in a cosmetic carrier, where the agent (B1) is free from CH-acidic compounds,
   (B2) an agent comprising at least one CH-acidic compound in a cosmetic carrier, where the agent (B2) is free from reactive carbonyl compounds, and where the at least one CH-acidic compound is selected from compounds of the formula (CH-1) and/or compounds of the formula (CH-2):

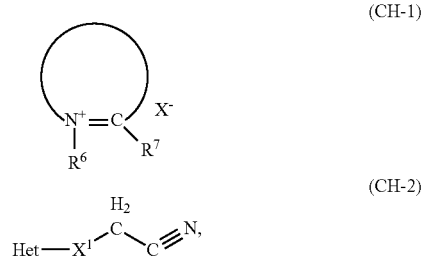

(CH-1)

(CH-2)

wherein $R^6$ represents a substituted or unsubstituted linear or cyclic ($C_1$ to $C_6$)alkyl group, ($C_2$ to $C_6$)alkenyl group, aryl group, heteroaryl group, or aryl($C_1$ to $C_6$)alkyl group, or a group of the formula $R^I R^{II} N$-$(CH_2)_m$-, in which m is an integer of from 2 to 6, and $R^I$ and $R^{II}$ are each independently H, a ($C_1$ to $C_4$)alkyl group, a ($C_1$ to $C_4$)hydroxyalkyl group, or an aryl-($C_1$ to $C_6$)alkyl group, or $R^I$ and $R^{II}$ together represent a $C_3$ to $C_6$ alkylene group that together with the nitrogen atom form a 5-, 6-, or 7-membered ring; $R^7$ represents a ($C_1$ to $C_6$)alkyl group; $X^-$ is a physiologically compatible anion; Het represents an optionally substituted heteroaromatic group; and $X^1$ represents a covalent bond or a carbonyl group (C=O);and
   (B3) an agent comprising at least one alkalizing agent;
(4) treating the colored hair of (2) with the CH-acidic hair dyeing agent (B) prepared in (3) to give a dyed hair; and
(5) treating the dyed hair of (4) with a cosmetic decolorizing agent (Ox) to give a multitonal dyed hair, wherein the cosmetic decolorizing agent (Ox) has a pH value in the range from 4 to 11, measured at 22° C., and comprises water and from about 0.5 to about 12 wt. % hydrogen peroxide, based on the total weight of the decolorizing agent (Ox).

17. The process of claim 16, wherein: (i) the preparation step (1) is carried out immediately before the treatment step (2); (ii) the preparation step (3) is carried out immediately before the treatment step (4); (iii) the treatment step (4) is carried out after a time interval of from about 1 minute to about 1.5 months subsequent to the treatment step (2); (iv) the treatment step (5) is carried out after a time interval of from about 1 minute to about 1.5 months subsequent to the treatment step (4); or (v) any combination of (i)-(iv).

18. The process of claim 16, wherein in the preparation step (1): (i) the developer component comprises at least one of p-phenylenediamine, p-toluylenediamine, 2-(beta-hydroxyethyl)-p-phenylenediamine, 2-methoxymethyl-p-phenylenediamine, 2-(alpha, beta-dihydroxyethyl)-p-phenylenediamine, N,N-bis-(beta-hydroxyethyl)-p-phenylenediamine, N-(4-amino-3-methylphenyl)-N43-(1H-imidazol-1-yl)propyl] amine, N,N'-bis-(b eta-hydroxy ethyl)-N,N'-b i s-(4-aminophenyl)-1,3-diamino-propan-2-ol, bis-(2-hydroxy-5-aminophenyl)-methane, 1,3-bis-(2,5-diaminophenoxy)-propan-2-ol, N,N'-bis-(4-aminophenyl)-1,4-diazacycloheptane, 1, 10-bis-(2,5-diaminophenyl)-1,4,7, 10-tetraoxadecane, p-aminophenol, 4-amino-3-methylphenol, 4-amino-2-aminomethylphenol, 4-amino-2-(alpha, beta-dihydroxyethyl)-phenol and 4-amino-2-(diethylaminomethyl)-phenol, 4,5-diamino-1-(beta-hydroxyethyl)-pyrazole, 2,4,5,6-tetraaminopyrimidine, 4-hydroxy-2,5,6-triaminopyrimidine, 2-hydroxy-4,5,6-triaminopyrimidine, and physiologically tolerated salts thereof; (ii) the coupler component comprises at least one of m-aminophenol, 5-amino-2-methylphenol, 3-amino-2-chloro-6-methyl phenol, 2-hydroxy-4-aminophenoxy ethanol, 5-amino-4-chloro-2-methyl phenol, 5-(2'-hydroxyethyl) amino-2-methylphenol, 2,4-dichloro-3-aminophenol, o-aminophenol, m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl} amino)ethanol, 2-({3-[(2-hydroxyethyl)amino]-2-methoxy-5-methylphenyl} amino) ethanol, 2-({3-[(2-hydroxyethyl)amino]-4,5-dimethylphenyl} amino)ethanol, 2-[3-morpholin-4-ylphenyl)amino] ethanol, 3-amino-4-(2-methoxyethoxy)-5-methylphenyl amine, 1-amino-3-bis-(2'-hydroxyethyl)-aminobenzene, Resorcinol, 2-methylresorcinol, 4-chlororesorcinol, 1,2,4-trihydroxybenzene, 2-amino-3-hydroxypyriadine, 3-amino-2-methyl amino-6-methoxypyriadine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthal ene, 2, 7-dihydroxynaphthal ene, 1,7-dihydroxynaphthal ene, 1, 8-dihydroxynaphthalene, 4-hydroxyindole, 6-hydroxyindole, 7-hydroxyindole, 4-hydroxyindoline, 6-hydroxyindoline, 7-hydroxyindoline, and physiologically tolerated salts thereof; (iii) the oxidizing agent comprises hydrogen peroxide; or (iv) any combination of (i)-(iii).

19. The process of claim 16, wherein the agent (B1) comprises: (i) a pH of from about 2 to about 5, measured at 22° C.; (ii) a reactive carbonyl compound selected from 4-hydroxy-2-methoxybenzaldehyde, 2-chloro-3,4-dihydroxybenzaldehyde, 2-b rom o-3,4-dihydroxybenzaldehyde, 3,4-dihydroxy-5-methoxybenzaldehyde, 2,3-di hydro-1,5-dimethyl-3-oxo-2-phenyl-1H-pyrazol e-4-carboxaldehyde, 2,4-dimethoxybenzaldehyde, 4-formyl-1-methylquinolinium-p-toluenesulfonate, and combinations thereof; or (iii) both (i) and (ii).

20. The process of claim 16, wherein the agent (B2) comprises: (i) a pH of from about 0.5 to about 3, measured at 22° C.; (ii) a salt of 1-allyl-1,2-dihydro-3,4,6-trim ethyl-2-oxo-pyrimidinium, and optionally additionally 1H-benzimidazol-2-ylacetonitrile (2-(cyanomethyl)benzimidazole); or (iii) both (i) and (ii).

\* \* \* \* \*

UNITED STATES PATENT AND TRADEMARK OFFICE
CERTIFICATE OF CORRECTION

PATENT NO. : 11,918,671 B2
APPLICATION NO. : 17/782090
DATED : March 5, 2024
INVENTOR(S) : Constanze Kruck et al.

It is certified that error appears in the above-identified patent and that said Letters Patent is hereby corrected as shown below:

In the Specification

Column 24, Line 10 change "$C_{12}$-22" to --$C_{12-22}$--.

Column 24, Line 12 change "$C_8$-22" to --$C_{8-22}$--.

Signed and Sealed this
Thirtieth Day of July, 2024

Katherine Kelly Vidal
*Director of the United States Patent and Trademark Office*